United States Patent
Wang et al.

(10) Patent No.: US 11,766,179 B2
(45) Date of Patent: Sep. 26, 2023

(54) DETERMINING FLOW SPEED AND/OR OXYGEN SATURATION BASED ON PHOTOACOUSTIC IMAGING AND SENSING

(71) Applicant: City University of Hong Kong, Kowloon (HK)

(72) Inventors: Lidai Wang, Kowloon (HK); Chao Liu, Kowloon (HK)

(73) Assignee: City University of Hong Kong, Kowloon (HK)

( * ) Notice: Subject to any disclaimer, the term of this patent is extended or adjusted under 35 U.S.C. 154(b) by 414 days.

(21) Appl. No.: 16/926,965

(22) Filed: Jul. 13, 2020

(65) Prior Publication Data
US 2022/0007944 A1    Jan. 13, 2022

(51) Int. Cl.
| | | |
|---|---|---|
| *A61B 5/00* | (2006.01) | |
| *G01N 29/24* | (2006.01) | |
| *A61B 5/026* | (2006.01) | |
| *A61B 8/12* | (2006.01) | |
| *A61B 5/145* | (2006.01) | |
| *G16H 50/50* | (2018.01) | |
| *G16H 50/30* | (2018.01) | |
| *G01N 29/44* | (2006.01) | |

(52) U.S. Cl.
CPC .......... *A61B 5/0095* (2013.01); *A61B 5/0261* (2013.01); *A61B 5/14542* (2013.01); *A61B 8/12* (2013.01); *G01N 29/2418* (2013.01); *G01N 29/4418* (2013.01); *G16H 50/30* (2018.01); *G16H 50/50* (2018.01); *G01N 2291/02466* (2013.01); *G01N 2291/02836* (2013.01)

(58) Field of Classification Search
CPC . A61B 5/0095; A61B 5/0261; A61B 5/14542; A61B 8/12; G16H 50/50; G16H 50/30; G01N 29/2418; G01N 29/4418; G01N 2291/02466; G01N 2291/02836
See application file for complete search history.

(56) References Cited

U.S. PATENT DOCUMENTS

| | | | | |
|---|---|---|---|---|
| 2009/0138215 | A1* | 5/2009 | Wang | G01F 1/704 |
| | | | | 702/48 |
| 2013/0102865 | A1* | 4/2013 | Man | G01N 21/1702 |
| | | | | 600/328 |
| 2015/0122033 | A1* | 5/2015 | Kim | G01N 21/1702 |
| | | | | 385/33 |

(Continued)

OTHER PUBLICATIONS

Menacho et al., Arterial pulse attenuation prediction using the decaying rate of a pressure wave in a viscoelastic material model, Biomech Model Mechanobiol (2018) 17:589-603, https://doi.org/10.1007/s10237-017-0980-9 (Year: 2018).*

(Continued)

*Primary Examiner* — John Denny Li
(74) *Attorney, Agent, or Firm* — Renner Kenner Greive Bobak Taylor & Weber

(57) ABSTRACT

A method and a method for determining flow speed based on photoacoustic imaging or sensing. The method includes receiving multiple photoacoustic signals from a sample in response to transmission of multiple laser pulses of different wavelengths to the sample, and processing the photoacoustic signals based on a flow model that relates photoacoustic signals with flow speed to determine a flow speed of a liquid flow in the sample.

46 Claims, 10 Drawing Sheets
(7 of 10 Drawing Sheet(s) Filed in Color)

(56) References Cited

U.S. PATENT DOCUMENTS

| | | | |
|---|---|---|---|
| 2018/0177409 A1* | 6/2018 | Irisawa | A61B 5/0095 |
| 2018/0228377 A1* | 8/2018 | Abe | A61B 5/14542 |
| 2018/0303349 A1* | 10/2018 | Wang | A61B 5/0095 |
| 2020/0329974 A1* | 10/2020 | Fadhel | A61B 5/0095 |

OTHER PUBLICATIONS

Lidai Wang, Chi Zhang, and Lihong V. Wang, Grueneisen Relaxation Photoacoustic Microscopy, Phys. Rev. Lett. 113, 174301—Published Oct. 20, 2014 (Year: 2014).*

Wang L, Yao J, Maslov KI, Xing W, Wang LV. Ultrasound-heated photoacoustic flowmetry. J Biomed Opt. Nov. 2013;18(11):117003. doi: 10.1117/1.JBO.18.11.117003. PMID: 24194064; PMCID: PMC4030689 (Year: 2013).*

B. Fagrell, M. Intaglietta, Microcirculation: its significance in clinical and molecular medicine, J. Intern. Med. 241 (1997) 349-362.

E. Macé, G. Montaldo, I. Cohen, M. Baulac, M. Fink, M. Tanter, Functional ultrasound imaging of the brain, Nat. Methods. 8(2011) 662.

D.M. Brizel, B. Klitzman, J.M. Cook, J. Edwards, G. Rosner, M.W. Dewhirst, A comparison of tumor and normal tissue microvascular hematocrits and red cell fluxes in a rat window chamber model, Int. J. Radiat. Oncol. 25 (1993) 269-276.

W.S. Kamoun, S.-S. Chae, D.A. Lacorre, J.A. Tyrrell, M. Mitre, M.A. Gillissen, D. Fukumura, R.K. Jain, L.L. Munn, Simultaneous measurement of RBC velocity, flux, hematocrit and shear rate in vascular networks, Nat. Methods. 7 (2010) 655.

D. Kleinfeld, P.P. Mitra, F. Helmchen, W. Denk, Fluctuations and stimulus-induced changes in blood flow observed in individual capillaries in layers 2 through 4 of rat neocortex, Proc. Natl. Acad Sci. 95 (1998) 15741-15746.

T.A. Woolsey, C.M. Rovainen, S.B. Cox, M.H. Henegar, G.E. Liang, D. Liu, Y.E. Moskalenko, J. Sui, L. Wei, Neuronal units linked to microvascular modules in cerebral cortex: response elements for imaging the brain, Cereb. Cortex. 6 (1996) 647-660.

D.E. McMillan, The Effect of Diabetes on Blood Flow Properties, Diabetes. 32 (1983) 56 LP-63.

X.-H. Zhu, J.M. Chen, T.-W. Tu, W. Chen, S.-K. Song, Simultaneous and noninvasive imaging of cerebral oxygen metabolic rate, blood flow and oxygen extraction fraction in stroke mice, Neuroimage. 64 (2013) 437-447.

H. Matsuda, Cerebral blood flow and metabolic abnormalities in Aizheimer's disease, 15 (2001) 85-92.

H. Fang, K. Maslov, L. V Wang, Photoacoustic Doppler effect from flowing small light-absorbing particles, Phys. Rev. Lett. 99 (2007) 184501.

L. Wang, K. Maslov, J. Yao, B. Rao, L. V Wang, Fast voice-coil scanning optical-resolution photoacoustic microscopy, Opt. Lett. 36 (2011) 139-141.

J. Yao, K.I. Maslov, Y. Shi, L.A. Taber, L. V Wang, In vivo photoacoustic imaging of transverse blood flow by using Doppler broadening of bandwidth, Opt. Lett. 35 (2010) 1419-1421.

L. Wang, K. Maslov, L. V Wang, Single-cell label-free photoacoustic flowoxigraphy in vivo, Proc. Natl. Acad. Sci. 110 (2013) 5759-5764.

H. Fang, K. Maslov, L. V Wang, Photoacoustic Doppler flow measurement in optically scattering media, Appl. Phys. Lett. 91 (2007) 264103.

J. Shi, L. V Wang, Bessel-beam Grueneisen relaxation photoacoustic microscopy with extended depth of field, J. Biomed. Opt. 20 (2015) 116002.

J. Yao, R. Gilson, K.I. Maslov, L. Wang, L. V Wang, Calibration-free structured-illumination photoacoustic flowgraphy of transverse flow in scattering media, J. Biomed. Opt. 19 (2014) 46007.

J. Brunker, P. Beard, Velocity measurements in whole blood using acoustic resolution photoacoustic Doppler, Biomed. Opt. Express. 7 (2016) 2789-2806.

R. Zhang, J. Yao, K.I. Maslov, L. V Wang, Structured-illumination photoacoustic Doppler flowmetry of axial flow in homogeneous scattering media, Appl. Phys. Lett. 103 (2013) 94101.

J. Yao, L. V Wang, Transverse flow imaging based on photoacoustic Doppler bandwidth broadening, J. Biomed. Opt. 15 (2010) 021304.

S. Chen, Z. Xie, P.L. Carson, X. Wang, L.J. Guo, In vivo flow speed measurement of capillaries by photoacoustic correlation spectroscopy, Opt Lett 36 (2011) 4017-4019.

S.-L. Chen, T. Ling, S.-W. Huang, H.W. Baac, L.J. Guo, Photoacoustic correlation spectroscopy and its application to low-speed flow measurement, Opt. Lett. 35 (2010) 1200-1202.

B. Ning, M.J. Kennedy, A.J. Dixon, N. Sun, R. Cao, B.T. Soetikno, R. Chen, Q. Zhou, K.K. Shung, J.A. Hossack, Simultaneous photoacoustic microscopy of microvascular anatomy, oxygen saturation, and blood flow, Opt. Lett. 40 (2015) 910-913.

A. Sheinfeld, A. Eyal, Photoacoustic thermal diffusion flowmetry, Biomed. Opt. Express. 3 (2012) 2610-2612.

L. Wang, K.I. Maslov, L. V Wang, Ultrasound-heated photoacoustic flowmetry, J. Biomed. Opt. 18 (2013) 117003.

R. Zhang, L. Wang, J. Yao, C.-H. Yeh, L. V Wang, In vivo optically encoded photoacoustic flowgraphy, Opt. Lett. 39 (2014) 3814-3817.

W. Liu, B. Lan, L. Hu, R. Chen, Q. Zhou, J. Yao, Photoacoustic thermal flowmetry with a single light source, J. Biomed. Opt. 22(2017) 96001.

P. Hajireza, A. Forbrich, R.J. Zemp, Multifocus optical-resolution photoacoustic microscopy using stimulated Raman scattering and chromatic aberration., Opt. Lett. 38 (2013) 2711-3.

P. Hajireza, A. Forbrich, R. Zemp, In-Vivo functional optical-resolution photoacoustic microscopy with stimulated Raman scattering fiber-laser source, Biomed. Opt. Express. 5 (2014) 539.

L. Xu, S. Alam, Q. Kang, D.P. Shepherd, D.J. Richardson, Raman-shifted wavelength-selectable pulsed fiber laser with high repetition rate and high pulse energy in the visible, Opt. Express. 25 (2017) 351-356.

Y. Liang, L. Jin, B.-O. Guan, L. Wang, 2 MHz multi-wavelength pulsed laser for functional photoacoustic microscopy, Opt. Lett. 42 (2017) 1452.

C. Liu, Y. Liang, L. Wang, Optical-resolution photoacoustic microscopy of oxygen saturation with nonlinear compensation, Biomed. Opt. Express. 10 (2019) 3061-3069.

L. Wang, C. Zhang, L. V Wang, Grueneisen relaxation photoacoustic microscopy, Phys. Rev. Lett. 113 (2014) 174301.

J. Ma, J. Shi, P. Hai, Y. Zhou, L. V Wang, Grueneisen relaxation photoacoustic microscopy in vivo, J. Biomed. Opt. 21 (2016) 66005.

M. Pramanik, L. V Wang, Thermoacoustic and photoacoustic sensing of temperature, J. Biomed. Opt. 14 (2009) 54024.

J. Shah, S. Park, S.R. Aglyamov, T. Larson, L. Ma, K. V Sokolov, K.P. Johnston, T.E. Milner, S.Y. Emelianov, Photoacoustic imaging and temperature measurement for photothermal cancer therapy, J. Biomed. Opt. 13 (2008) 34024.

L. V Wang, Wu Hi Biomedical Optics: Principles and Imaging, (2007) Hoboken, N.J.: Wiley-Interscience.xiv,362.

M. Xu, L. V. Wang, Photoacoustic imaging in biomedicine, Rev. Sci. Instrum. 77 (2006).

K. Maslov, H.F. Zhang, L. V. Wang, Effects of wavelength-dependent fluence attenuation on the noninvasive photoacoustic imaging of hemoglobin oxygen saturation in subcutaneous vasculature in vivo, Inverse Probl. 23 (2007).

J.T. Murray, W.L. Austin, R.C. Powell, Intracavity Raman conversion and Raman beam cleanup, Opt. Mater. (Amst). 11 (1999) 353-371.

S.H. Baek, W.B. Roh, Single-mode Raman fiber laser based on a multimode fiber, Opt. Lett. 29 (2004) 153-155.

H. Pourbeyram, G.P. Agrawal, A. Mafi, SRS-mediated generation of new wavelengths from 523 nm to 1750 nm in a graded-index multimode optical fiber, in: CLEO Sci. Innov., Optical Society of America, 2013: pp. CTu2E-7.

K.S. Chiang, Stimulated Raman scattering in a multimode optical fiber: evolution of modes in Stokes waves, Opt. Lett. 17 (1992) 352-354.

(56) References Cited

OTHER PUBLICATIONS

M. Minderer, W. Liu, L.T. Sumanovski, S. Kugler, F. Helmchen, D.J. Margolis, Chronic imaging of cortical sensory map dynamics using a genetically encoded calcium indicator, J. Physiol. 590 (2012) 99-107.

D. Ho, X. Zhao, S. Gao, C. Hong, D.E. Vatner, S.F. Vatner, Heart rate and electrocardiography monitoring in mice, Curr. Protoc. Mouse Biol. 1 (2011) 123-139. S. Jeon, J. Kim, D. Lee, J.W. Baik, C. Kim, Review on practical photoacoustic microscopy, Photoacoustics. 15 (2019) 100141.

S. Jeon, J. Kim, D. Lee, J.W. Baik, C. Kim, Review on practical photoacoustic microscopy, Photoacoustics. 15 (2019) 100141.

M.J. Moore, S. El-Rass, Y. Xiao, Y. Wang, X.-Y. Wen, M.C. Kolios, Simultaneous ultra-high frequency photoacoustic microscopy and photoacoustic radiometry of zebrafish larvae in vivo, Photoacoustics. 12 (2018) 14-21.

W. Liu, J. Yao, Photoacoustic microscopy: principles and biomedical applications, Biomed. Eng. Lett. 8 (2018) 203-213.

G. Agrawal, Chapter 8—Stimulated Raman Scattering, in: G.B.T.-N.F.O. (Fifth E. Agrawal (Ed.), Opt. Photonics, Academic Press, Boston, 2013: pp. 295-352.

\* cited by examiner

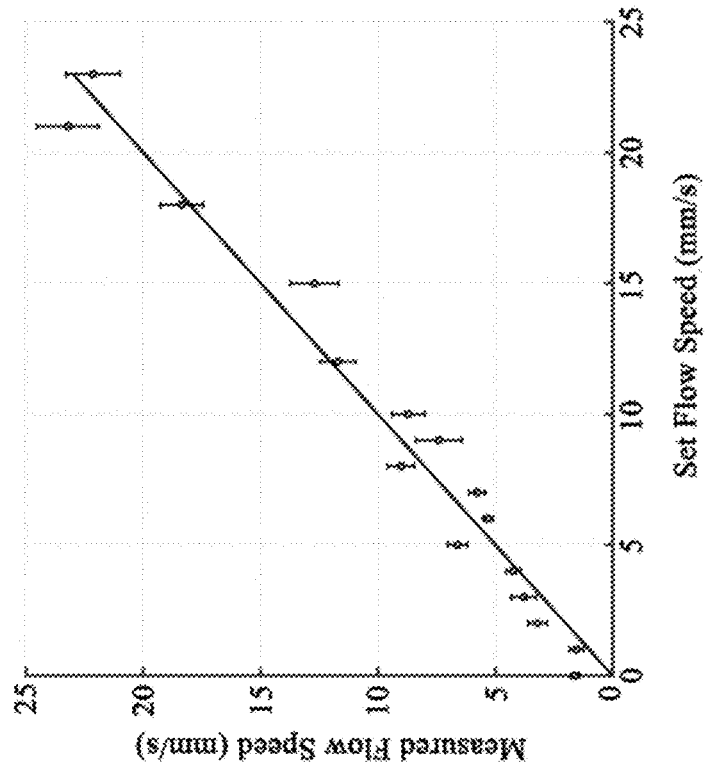
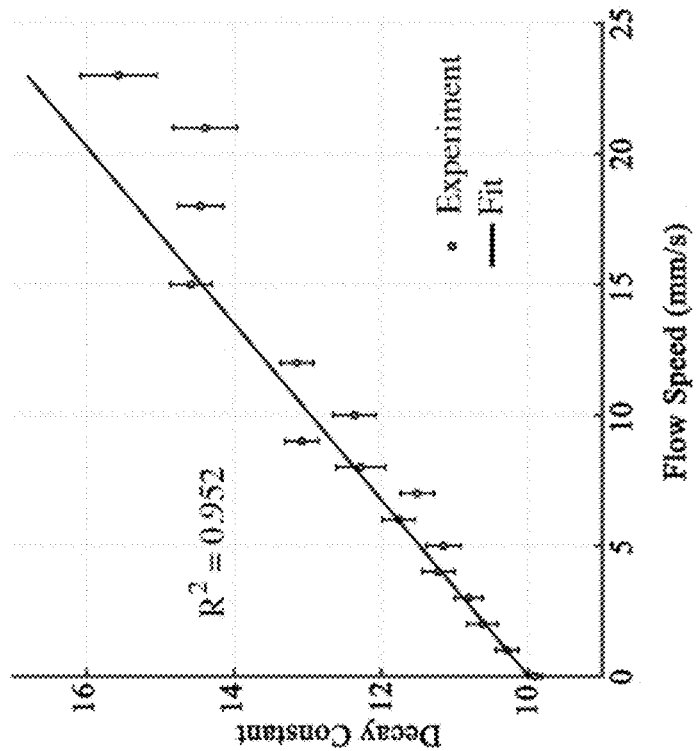
Figure 3A
Figure 3B

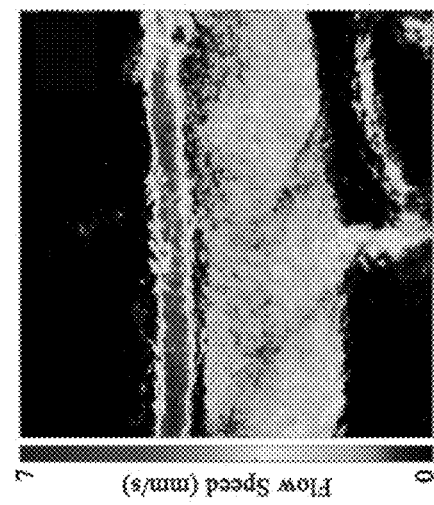
Figure 4A
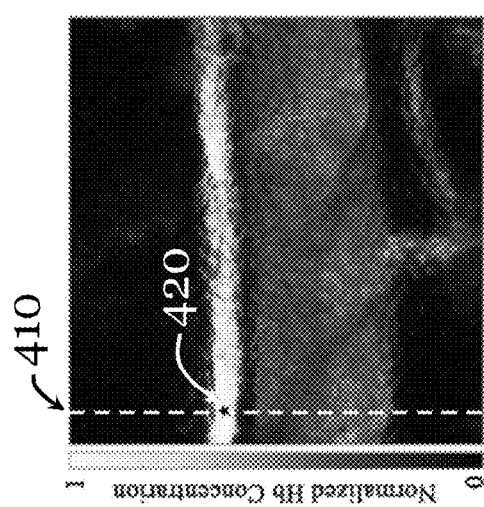
Figure 4B
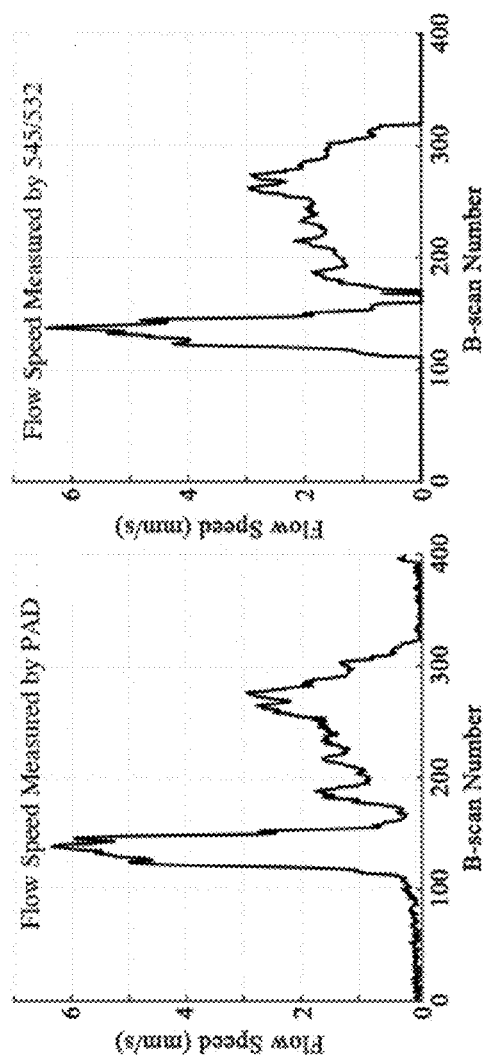
Figure 4C
Figure 4D

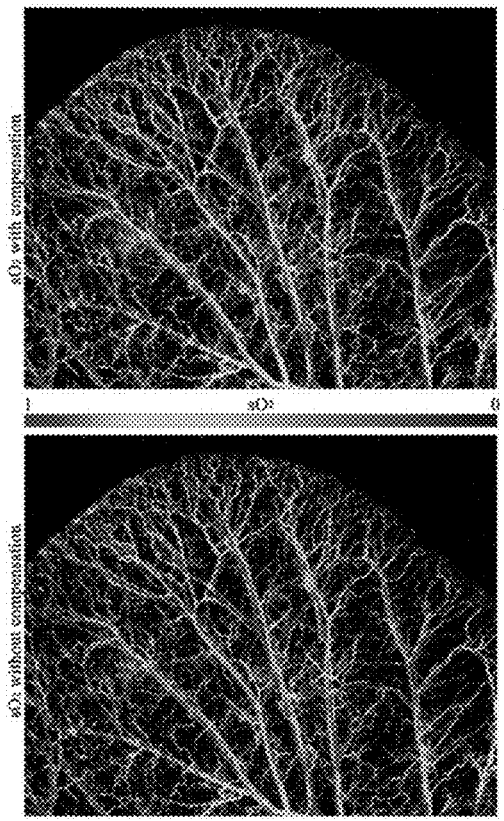
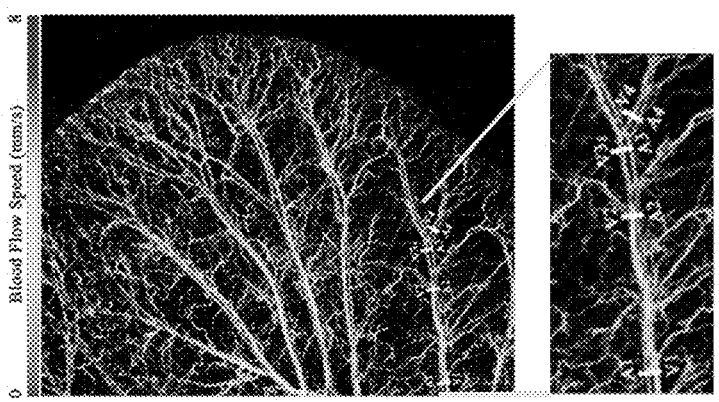
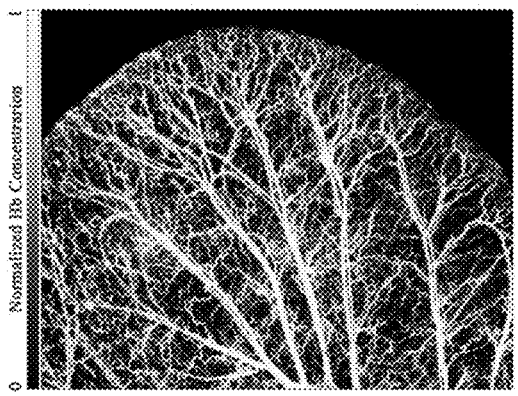
Figure 5A  Figure 5B  Figure 5C  Figure 5D

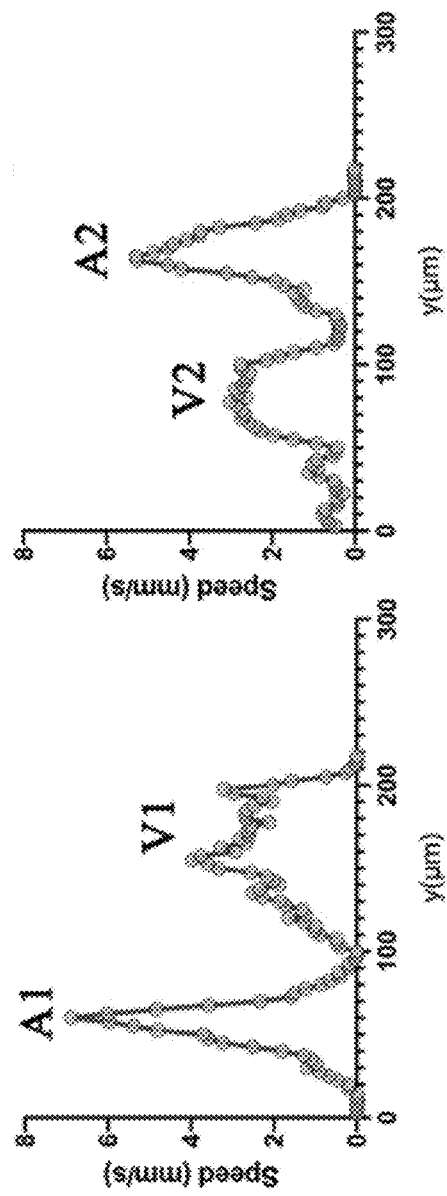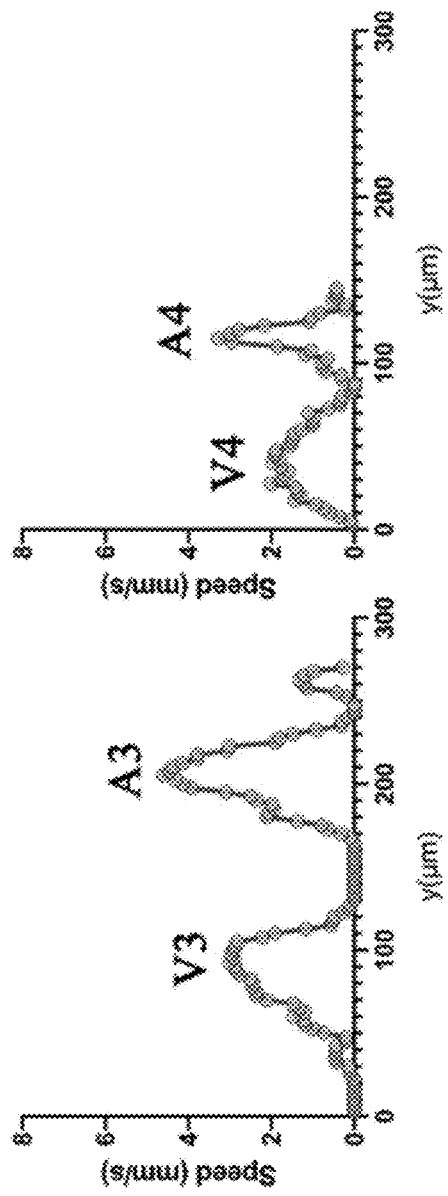
Figure 6A Figure 6B Figure 6C Figure 6D

DETERMINING FLOW SPEED AND/OR OXYGEN SATURATION BASED ON PHOTOACOUSTIC IMAGING AND SENSING

TECHNICAL FIELD

The invention relates to a system and a method for determining flow speed and/or oxygen saturation based on photoacoustic imaging/sensing. The invention also relates to a related photoacoustic imaging/sensing apparatus.

BACKGROUND

Photoacoustic imaging is a biomedical imaging modality based on the use of laser-generated ultrasound, and it is considered as one of the most promising imaging techniques to have emerged in recent years. In general, photoacoustic imaging is based on absorption of laser light by specific tissue chromophores to excite ultrasound waves. These ultrasonic waves are encoded with optical properties of the tissue. By recording these waves over the tissue surface, a 3D absorption based image can be reconstructed.

Apart from obtaining anatomical images, photoacoustic imaging can also be applied to perform functional imaging, such as in functional optical-resolution photoacoustic microscopy (OR-PAM), to determine functional properties of the tissues. One properties of particular interest is flow speed of body liquid such as blood. Existing methods to measure blood flow speed are based on various approaches, including photoacoustic Doppler (PAD), photoacoustic correlation spectroscopy (PACS), and thermal diffusion flowmetry (TDF). While each of these methods has their own advantages, they all require tens to hundreds of photoacoustic measurements to calculate the flow speed, which is time-consuming and computationally inefficient.

SUMMARY OF THE INVENTION

In accordance with a first aspect of the invention, there is provided a method for determining flow speed based on photoacoustic imaging or sensing. The method includes receiving multiple photoacoustic signals (e.g., a first photoacoustic signal and a second photoacoustic signal) from a sample in response to transmission of multiple laser pulses (e.g., a first laser pulse and a second laser pulse) to the sample; and processing the first photoacoustic signal and the second photoacoustic signal based on a flow model that relates photoacoustic signals with flow speed to determine a flow speed of a liquid flow in the sample. The first pulse laser has a first wavelength and the second laser pulse has a second wavelength different from the first wavelength. Preferably, the method is performed using one or more processors, optionally at least partly incorporated in a photoacoustic imaging or sensing apparatus. The one or more processors may be arranged on the same apparatus, or arranged distributively on a computing network. The sample may be placed in or on a holder or support of the photoacoustic imaging or sensing apparatus.

In one embodiment of the first aspect, the processing includes determining the amplitudes of multiple photoacoustic signals; and applying the determined amplitudes to the flow model. For example, the processing includes determining a first amplitude of the first photoacoustic signal and a second amplitude of the second photoacoustic signal; and applying the first and second amplitudes to the flow model.

In one embodiment of the first aspect, the flow model is an exponential decay model.

In one embodiment of the first aspect, the flow model relates the first and second amplitude with flow speed by:

$$P_2 = \frac{F_2 \mu_{a2}}{F_1 \mu_{a1}} P_1 + \frac{F_2 \mu_{a2}}{F_1 \mu_{a1}} P_1^2 A e^{-(\tau_\alpha + bv)\delta t}$$

where $P_1$ is the first amplitude, $P_2$ is the second amplitude, $F_1$ and $F_2$ are optical fluences associated with the first and second laser pulses, $\mu_{a1}$ and $\mu_{a2}$ are the optical absorption coefficients associated with the first and second laser pulses, A, $\tau_\alpha$, and b are coefficients independent of the flow, $\delta t$ is a time delay between the first and second laser pulses, $v$ is the flow speed.

In one embodiment of the first aspect, the method further includes transmitting the first laser pulse and the second laser pulse to the sample. The transmission may be performed using a probe connected to or of a photoacoustic imaging or sensing apparatus.

In some embodiments of the first aspect, the time difference between transmission of the first and second laser pulses may be in the order of nano-seconds, in the order of micro-seconds, in the order of milli-seconds, or etc.

In one embodiment of the first aspect, the first wavelength of the first laser pulse and the second wavelength of the second laser pulse are isosbestic wavelengths, e.g., for blood.

In one embodiment of the first aspect, the method further includes processing one of the first photoacoustic signal and the second photoacoustic signal based on a photoacoustic absorption model to determine particulate concentration in liquid.

In one embodiment of the first aspect, the sample is a human or animal. In one embodiment of the first aspect, the method is performed in vivo. In one embodiment of the first aspect, the liquid is one or more of: blood, lymphatic fluid, etc. The sample may alternatively be a phantom, a dead object, etc.

In one embodiment of the first aspect in which the liquid is blood, the method also includes processing one of the first photoacoustic signal and the second photoacoustic signal based on a photoacoustic absorption model to determine hemoglobin concentration in the blood.

In one embodiment of the first aspect in which the liquid is blood, the method includes receiving a third photoacoustic signal from a sample in response to transmission of a third laser pulse to the sample, the third laser pulse has a third wavelength different from the first wavelength and the second wavelength; and processing at least one of the first photoacoustic signal and the second photoacoustic signal, and the third photoacoustic signal, based on a linear spectral unmixing model to determine oxygen saturation in the blood. The determined oxygen saturation can be uncompensated oxygen saturation in the blood or compensated oxygen saturation in the blood.

In one embodiment of the first aspect, the first, second, and third laser pulses are transmitted sequentially, e.g., from the same laser source, and in such a way that a time difference between transmission of the first and second laser pulses is in the order of micro-seconds or sub-microseconds, and a time difference between transmission of the second and third laser pulses is in the order of micro-seconds or sub-microseconds. The two time differences (between adjacent laser pulses) may be different or the same.

In one embodiment of the first aspect, the processing includes determining a first amplitude of the first photoacoustic signal and a third amplitude of the third photoacoustic signal; and applying the first and third amplitudes to the linear spectral unmixing model. The linear spectral unmixing model may be represented by:

$$sO_2 = \frac{\varepsilon_{\lambda_3}^{de} - r\varepsilon_{\lambda_1}^{de}}{\left(\varepsilon_{\lambda_3}^{de} - \varepsilon_{\lambda_3}^{oxy}\right) - r\left(\varepsilon_{\lambda_1}^{de} - \varepsilon_{\lambda_1}^{oxy}\right)}$$

where $sO_2$ is the (e.g., uncompensated) oxygen saturation in the blood, $$r = \frac{\mu_{a3}}{\mu_{a1}} = \frac{P_3 F_1}{P_1 F_3},$$

$P_1$ and $P_3$ are the first and third amplitudes, $F_1$ and $F_3$ are optical fluences associated with the first and third laser pulses, $\varepsilon_{\lambda_{1,3}}^{de}$ and $\varepsilon_{\lambda_{1,3}}^{oxy}$ are molar extinction coefficients of oxyhemoglobin and deoxyhemoglobin at the first and third wavelengths.

In one embodiment of the first aspect, the processing includes processing the first amplitude of the first photoacoustic signal, the second amplitude of the second photoacoustic signal, and the third amplitude of the third photo acoustic signal based on the linear spectral unmixing model; and applying the first, second, and third amplitudes to the linear spectral unmixing model. The linear spectral unmixing model may be a compensated model that relates photoacoustic signals with oxygen saturation, taking into account errors in the photoacoustic signals (e.g., caused by the Grüneisen relaxation effect). For example, the linear spectral unmixing model can be represented by:

$$sO_2 = \frac{\varepsilon_{\lambda_3}^{de} - r'\varepsilon_{\lambda_1}^{de}}{\left(\varepsilon_{\lambda_3}^{de} - \varepsilon_{\lambda_3}^{oxy}\right) - r'\left(\varepsilon_{\lambda_1}^{de} - \varepsilon_{\lambda_1}^{oxy}\right)}$$

where $sO_2$ is the (e.g., compensated) oxygen saturation in the blood, $$r' = \frac{P_3 F_1}{P_1 F_3} \cdot \frac{1}{1 + AP_1 e^{-(\tau_\alpha + bv)2\delta t} + AP_1 \frac{F_2 \mu_{a2}}{F_1 \mu_{a1}} e^{-(\tau_\alpha + bv)\delta t}},$$

$P_1$, $P_2$, and $P_3$ are the first, second, and third amplitudes, $F_1$ and $F_3$ are optical fluences associated with the first and third laser pulses, $\delta t$ is a time delay between the first and second laser pulses, as well as a time delay between the second and third laser pulses, A, $\tau_\alpha$, and b are coefficients independent of the flow, $\mu_{a1}$ and $\mu_{a2}$ are the optical absorption coefficients associated with the first and second laser pulses, $\varepsilon_{\lambda_{1,3}}^{de}$ and $\varepsilon_{\lambda_{1,3}}^{oxy}$ are molar extinction coefficients of oxyhemoglobin and deoxyhemoglobin at the first and third wavelengths.

In accordance with a second aspect of the invention, there is provided a non-transitory computer readable medium storing computer instructions that, when executed by one or more processors, are arranged to cause the one or more processors to perform the method of the first aspect. The one or more processors may be arranged on the same apparatus, or arranged distributively on a computing network.

In accordance with a third aspect of the invention, there is provided an article including the computer readable medium of the second aspect.

In accordance with a fourth aspect of the invention, there is provided a computer program product storing instructions and/or data that are executable by one or more processors, the instructions and/or data are arranged to cause the one or more processors to perform the method of the first aspect.

In accordance with a fifth aspect of the invention, there is provided a system for determining flow speed based on photoacoustic imaging or sensing. The system includes one or more processors arranged to: receive multiple photoacoustic signals (e.g., a first photoacoustic signal and a second photoacoustic signal) from a sample in response to transmission of multiple laser pulses (e.g., a first laser pulse and a second laser pulse) to the sample, the first pulse laser has a first wavelength and the second laser pulse has a second wavelength different from the first wavelength, e.g., from the same laser source; and process the first photoacoustic signal and the second photoacoustic signal based on a flow model that relates photoacoustic signals with flow speed to determine a flow speed of a liquid flow in the sample. The model may be stored in a memory operably connected with the one or more processors.

In one embodiment of the fifth aspect, the one or more processors are arranged to: determine the amplitudes of multiple photoacoustic signals and apply the determined amplitudes to the flow model. For example, the one or more processors are arranged to determine a first amplitude of the first photoacoustic signal and a second amplitude of the second photoacoustic signal; and apply the first and second amplitudes to the flow model.

In one embodiment of the fifth aspect, the flow model is an exponential decay model.

In one embodiment of the fifth aspect, the flow model relates the first and second amplitude with flow speed by:

$$P_2 = \frac{F_2 \mu_{a2}}{F_1 \mu_{a1}} P_1 + \frac{F_2 \mu_{a2}}{F_1 \mu_{a1}} P_1^2 A e^{-(\tau_\alpha + bv)\delta t}$$

where $P_1$ is the first amplitude, $P_2$ is the second amplitude, $F_1$ and $F_2$ are optical fluences associated with the first and second laser pulses, $\mu_{a1}$ and $\mu_{a2}$ are the optical absorption coefficients associated with the first and second laser pulses, A, $\tau_\alpha$, and b are coefficients independent of the flow, $\delta t$ is a time delay between the first and second laser pulses, v is the flow speed.

In one embodiment of the fifth aspect, the system further includes a photoacoustic imaging or sensing apparatus having a probe arranged to transmit the first laser pulse and the second laser pulse to the sample. The photoacoustic imaging or sensing apparatus may include the one or more processors, or at least part of the one or more processors. The probe is arranged to transmit the first and second laser pulses in such a way that the first and second laser pulses have a time difference in the order of nano-seconds, in the order of micro-seconds, in the order of milli-seconds, etc. In one example, the first wavelength of the first laser pulse and the second wavelength of the second laser pulse are isosbestic wavelengths, e.g., for blood.

In one embodiment of the fifth aspect, the one or more processors are arranged to process one of the first photoacoustic signal and the second photoacoustic signal based on a photoacoustic absorption model to determine particulate concentration in liquid.

In one embodiment of the fifth aspect, the sample is a human or animal. In one embodiment of the fifth aspect, the method is performed in vivo. In one embodiment of the fifth aspect, the liquid is one or more of: blood, lymphatic fluid, etc. The sample may alternatively be a phantom, a dead object, etc.

In one embodiment of the fifth aspect in which the liquid is blood, the one or more processors are arranged to process one of the first photoacoustic signal and the second photoacoustic signal based on a photoacoustic absorption model to determine hemoglobin concentration in the blood.

In one embodiment of the fifth aspect, the one or more processors are further arranged to receive a third photoacoustic signal from a sample in response to transmission of a third laser pulse to the sample, the third laser pulse has a third wavelength different from the first wavelength and the second wavelength; and process at least one of the first photoacoustic signal and the second photoacoustic signal, and the third photoacoustic signal, based on a linear spectral unmixing model to determine oxygen saturation in the blood. The determined oxygen saturation can be uncompensated oxygen saturation in the blood or compensated oxygen saturation in the blood.

In one embodiment of the fifth aspect, the probe of the photoacoustic imaging or sensing apparatus is arranged to transmit the first, second, and third laser pulses sequentially, and a time difference between transmission of the first and second laser pulses is in the order of micro-seconds or sub-microseconds, and a time difference between transmission of the second and third laser pulses is in the order of micro-seconds or sub-microseconds. The two time differences (between adjacent laser pulses) may be different or the same.

In one embodiment of the fifth aspect, the one or more processors are further arranged to determine a first amplitude of the first photoacoustic signal and a third amplitude of the third photoacoustic signal; and apply the first and third amplitudes to the linear spectral unmixing model. The linear spectral unmixing model may be represented by:

$$sO_2 = \frac{\varepsilon_{\lambda_3}^{de} - r\varepsilon_{\lambda_1}^{de}}{(\varepsilon_{\lambda_3}^{de} - \varepsilon_{\lambda_3}^{oxy}) - r(\varepsilon_{\lambda_1}^{de} - \varepsilon_{\lambda_1}^{oxy})}$$

where $sO_2$ is the (e.g., uncompensated) oxygen saturation in the blood, $$r = \frac{\mu_{a3}}{\mu_{a1}} = \frac{P_3 F_1}{P_1 F_3},$$

$P_1$ and $P_3$ are the first and third amplitudes, $F_1$ and $F_3$ are optical fluences associated with the first and third laser pulses, $\varepsilon_{\lambda_{1,3}}^{de}$ and $\varepsilon_{\lambda_{1,3}}^{oxy}$ are molar extinction coefficients of oxyhemoglobin and deoxyhemoglobin at the first and third wavelengths.

In one embodiment of the fifth aspect, the one or more processors are further arranged to process the first amplitude of the first photoacoustic signal, the second amplitude of the second photoacoustic signal, and a third amplitude of the third photoacoustic signal based on the linear spectral unmixing model; and apply the first, second, and third amplitudes to the linear spectral unmixing model. The linear spectral unmixing model may be a compensated model that relates photoacoustic signals with oxygen saturation, taking into account errors in the photoacoustic signals (e.g., caused by the Grüneisen relaxation effect). The linear spectral unmixing model may be represented by:

$$sO_2 = \frac{\varepsilon_{\lambda_3}^{de} - r'\varepsilon_{\lambda_1}^{de}}{(\varepsilon_{\lambda_3}^{de} - \varepsilon_{\lambda_3}^{oxy}) - r'(\varepsilon_{\lambda_1}^{de} - \varepsilon_{\lambda_1}^{oxy})}$$

where $sO_2$ is the (e.g., compensated) oxygen saturation in the blood, $$r' = \frac{P_3 F_1}{P_1 F_3} \cdot \frac{1}{1 + AP_1 e^{-(\tau_\alpha + bv)2\delta t} + AP_1 \frac{F_2 \mu_{a2}}{F_1 \mu_{a1}} e^{-(\tau_\alpha + bv)\delta t}},$$

$P_1$, $P_2$, and $P_3$ are the first, second, and third amplitudes, $F_1$ and $F_3$ are optical fluences associated with the first and third laser pulses, $\delta t$ is a time delay between the first and second laser pulses, as well as a time delay between the second and third laser pulses, $A$, $\tau_\alpha$, and $b$ are coefficients independent of the flow, $\mu_{a1}$ and $\mu_{a2}$ are the optical absorption coefficients associated with the first and second laser pulses, $\varepsilon_{\lambda_{1,3}}^{de}$ and $\varepsilon_{\lambda_{1,3}}^{oxy}$ are molar extinction coefficients of oxyhemoglobin and deoxyhemoglobin at the first and third wavelengths.

In accordance with a sixth aspect of the invention, there is provided a photoacoustic imaging or sensing apparatus including: a pulsed laser source; an optical processing unit operably connected with the pulsed laser source, the optical processing unit being arranged to process pulsed laser received from the pulsed laser source to provide laser pulses of different wavelengths; and a probe operably connected with the optical processing unit, for transmitting the laser pulses to a sample. The pulsed laser source may be a single-wavelength source arranged to provide laser pulses of only the first wavelength. The laser pulses may be nanosecond laser pulses. The laser pulses of different wavelengths may be temporally separated laser pulses.

In one embodiment of the sixth aspect, the optical processing unit includes: a first optical processing sub-unit arranged in a first optical path, arranged to provide a pulse laser of a first wavelength; a second optical processing sub-unit arranged in a second optical path arranged to provide a pulse laser of a second wavelength different from the first wavelength; a third optical processing sub-unit arranged in a third optical path arranged to provide a pulse laser of a third wavelength different from the first and second wavelengths. The first, second, and third optical paths may be arranged at least partly in parallel with each other.

In one embodiment of the sixth aspect, the first optical processing sub-unit includes a power adjuster arranged to adjust a power of the laser pulse provided by the pulsed laser source.

In one embodiment of the sixth aspect, the second optical processing sub-unit includes an optical regulator arranged to alter a wavelength of the laser pulse provided by the pulsed laser source by excitation based on stimulated Raman scattering and to introduce a time delay to the laser pulse provided by the pulsed laser source. The optical regulator may include a single-mode optical fiber. The single-mode optical fiber may be a polarization-maintaining single-mode optical fiber.

In one embodiment of the sixth aspect, the third optical processing sub-unit includes an optical regulator arranged to alter a wavelength of the laser pulse provided by the pulsed laser source by excitation based on stimulated Raman scattering and to introduce a time delay to the laser pulse provided by the pulsed laser source. The optical regulator may include a multi-mode optical fiber. The time delay introduced may be the same as the time delay introduced by the second optical processing sub-unit.

In one embodiment of the sixth aspect, the photoacoustic imaging or sensing apparatus can be used in the method of the first aspect and the system of the fifth aspect.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments of the invention will now be described, by way of example, with reference to the accompanying drawings in which:

FIG. 3A is a graph showing the variation of the decay constants (in the flow model of one embodiment) with flow speeds obtained during calibration of the system of FIG. 2A;

FIG. 3B is a graph showing the variation of the measured flow speed with predetermined flow speeds;

FIG. 4A is a photoacoustic image of blood vessels in a mouse ear acquired during an in vivo experiment using the system of FIG. 2A;

FIG. 4B is a flow speed image of the blood vessels obtained during the in vivo experiment using the system of FIG. 2A;

FIG. 4C is a graph showing a profile of flow speed along the dashed line of FIG. 4A as measured by an existing photoacoustic Doppler method;

FIG. 4D is a graph showing a profile of flow speed along the dashed line of FIG. 4A as measured by the dual-pulse method in one embodiment of the invention;

FIG. 5A is a large field-of-view photoacoustic image of microvascular structure of the mouse ear acquired during an in vivo experiment using the system of FIG. 2A;

FIG. 5B is flow speed image of the microvascular structure of the mouse ear acquired during an in vivo experiment using the system of FIG. 2A;

FIG. 5C is an oxygen saturation image (without compensation for errors in the photoacoustic signals) of the microvascular structure of the mouse ear acquired during an in vivo experiment using the system of FIG. 2A;

FIG. 5D is an oxygen saturation image (with compensation for the errors in the photoacoustic signals) of the microvascular structure of the mouse ear acquired during an in vivo experiment using the system of FIG. 2A;

FIG. 6A is a graph showing blood flow speed measured in selected artery-vein pairs labelled in FIG. 5B;

FIG. 6B is a graph showing blood flow speed measured in selected artery-vein pairs labelled in FIG. 5B;

FIG. 6C is a graph showing blood flow speed measured in selected artery-vein pairs labelled in FIG. 5B;

FIG. 6D is a graph showing blood flow speed measured in selected artery-vein pairs labelled in FIG. 5B;

DETAILED DESCRIPTION

Figure 1:
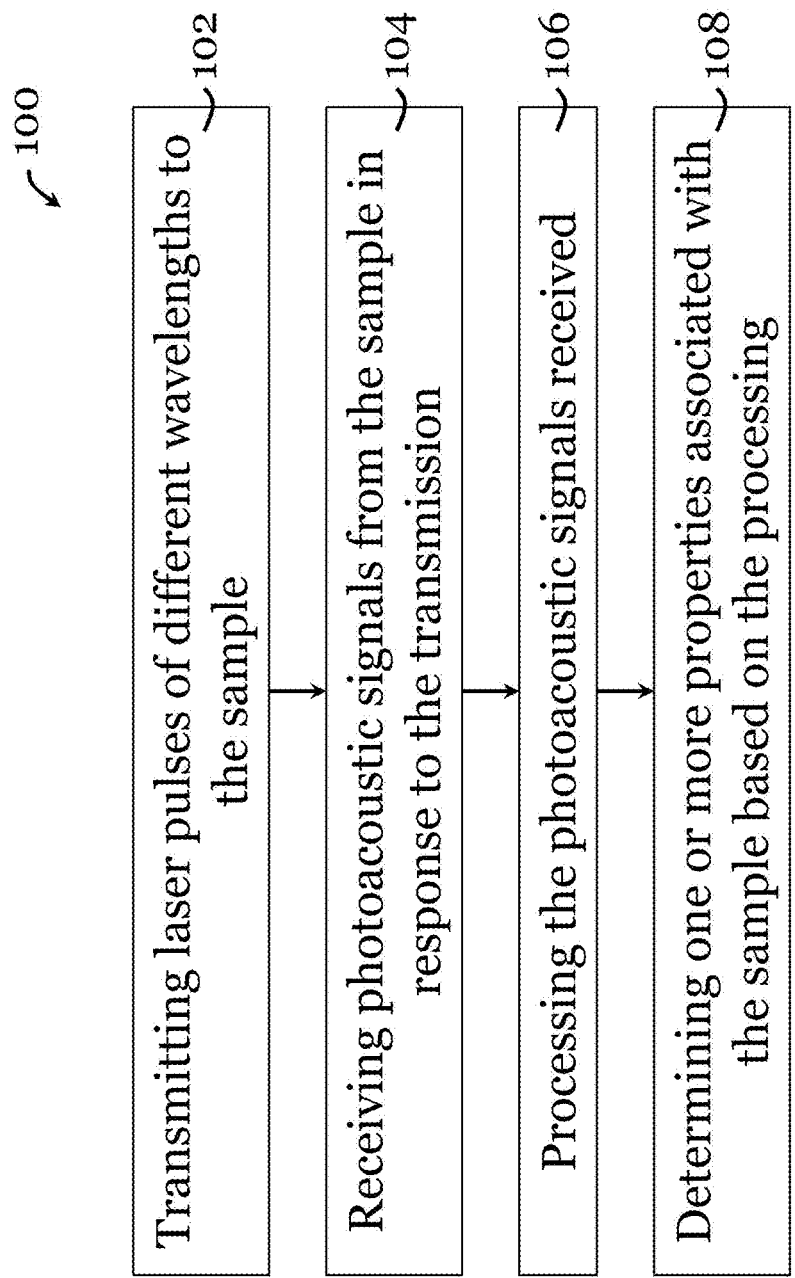
FIG. 1 is a flow chart showing a method for determining one or more properties based on photoacoustic imaging or sensing in one embodiment of the invention.

FIG. 1 illustrates a method too for determining one or more properties based on photoacoustic imaging or sensing in one embodiment of the invention. The method too begins in step 102, in which laser pulses of different wavelengths are transmitted to a sample. The sample may be a live object, such as a human or animal, or a dead object, such as a phantom, a device, an apparatus, etc. Then, in step 104, photoacoustic signals are received, e.g., by a probe of a photoacoustic imaging or sensing apparatus, from the sample in response to the transmission. Generally, one laser pulse excites one photoacoustic signal. In step 106, the photoacoustic signals received are processed by a processor. The processing may be based on different models, depending on the properties to be measured or calculated. After the processing, in step 108, one or more properties associated with the sample are determined. The determined properties may be displayed on a display, such as one operably connected with a processor, for view by the user. In one implementation, the method enables simultaneous determination of multiple properties based on a limited number of laser pulses. The method too may also include acquiring an image of the sample.

In one example, the property is blood flow speed (of the sample). In this example, step 102 includes transmitting two laser pulses of different wavelengths (e.g., isosbestic wavelengths) to the sample, and step 104 includes receiving two photoacoustic signals from the sample in response to transmission of the two laser pulses. The time difference between transmissions of the two laser pulses may be in the order of micro-seconds, in the order of nano-seconds, etc. Steps 106 and 108 may include determining respective amplitudes of the two photoacoustic signals and applying the determined amplitudes to a flow model that relates photoacoustic signals with flow speed, to determine the blood flow speed. The flow model takes into account errors in the photoacoustic signals (e.g., caused by the Grüneisen relaxation effect).

In one example, the property may further include hemoglobin concentration in the blood. In this example, steps 106 and 108 may include processing one of the two photoacoustic signals obtained during the blood flow speed measurement based on a photoacoustic absorption model to determine hemoglobin concentration in the blood.

In one example, the property may further include oxygen saturation in the blood. In this example, step 102 includes transmitting another laser pulse of different wavelength (compared to the other two laser pulses) to the sample, and step 104 includes receiving another photoacoustic signal from the sample in response to transmission of the other laser pulse. Each of the time differences between transmissions of the two laser pulses may be in the order of micro-seconds, in the order of nano-seconds, etc. The two time differences may be identical. Steps 106 and 108 may include processing at least one of the two photoacoustic signals, and the other photoacoustic signal, based on a linear spectral unmixing model to determine oxygen saturation in the blood. The linear spectral unmixing model may also take into account errors in the photoacoustic signal (e.g., caused by the Grüneisen relaxation effect).

In one implementation of the method 100, hemoglobin concentration, oxygen saturation, and blood flow can be determined with a single raster scan. Details of the determination of hemoglobin concentration, oxygen saturation, and blood flow are as follows.

A. Hemoglobin Concentration Measurement

In one embodiment, the hemoglobin concentration is determined based on a photoacoustic absorption model and oxygen saturation is determined based on a linear spectral unmixing method/model, illustrated Y. Liang, L. Jin, B.-O. Guan, L. Wang, 2 *MHz multi-wavelength pulsed laser for functional photoacoustic microscopy*, Opt. Lett. 42 (2017) 1452 and C. Liu, Y. Liang, L. Wang, *Optical-resolution photoacoustic microscopy of oxygen saturation with nonlinear compensation*, Biomed. Opt. Express. 10 (2019) 3061-3069.

B. Flow Measurement

In one embodiment, blood flow speed is determined using a dual-pulse method/model or multiple-pulse method/model (uses at least two pulses) in one embodiment of the invention. In photoacoustic imaging or sensing, the earlier photoacoustic excitation may affect the amplitudes of the latter photoacoustic signals. This dependency can change due to one or more of: diffusion, temperature, and flow. In the present embodiment, two or more photoacoustic signals with only sub-microseconds delay between adjacent signals is utilized for determining flow speed. The present embodiment hypothesizes that the blood flow can significantly affect the inter-pulse signal amplitude dependency in a short time delay. In this embodiment the relationship between the dual-pulse or multiple-pulse amplitudes and the blood flow speed is modelled. After calibration, the flow speed can be measured or determined from a set of photoacoustic measurements. The method in the present embodiment can be referred to as a dual-pulse flowmetric method.

In the dual-pulse flowmetric method, two short-delayed nanosecond laser pulses are transmitted to the sample to excite two photoacoustic signals. The time delay between the two laser pulses is $\delta t$. In linear range, the induced photoacoustic amplitudes $P_1$ and $P_2$ can be approximated as $$P_1 = k\Gamma_0 \eta F_1 \mu_{a1}$$

$$P_2 = k(\Gamma_0 + \Delta\Gamma)\eta F_2 \mu_{a2} \quad (1)$$

where k is the detection sensitivity, $\Gamma_0$ is a parameter related to photoacoustic excitation efficiency, $\Delta\Gamma$ is the increased parameter related to photoacoustic excitation efficiency at the second photoacoustic excitation, $\eta$ is the light-to-heat conversion coefficient, $F_1$ and $F_2$ are the optical fluences, and $\mu_{a1}$ and $\mu_{a2}$ are the optical absorption coefficients at the two laser wavelengths. In one embodiment, when two isosbestic wavelengths, i.e., 532 nm and 545 nm, are used, the absorption coefficients at the two wavelengths will be independent of oxygen saturation and $\mu_{a1}/\mu_{a2}$ is a known constant. In the second photoacoustic excitation, $\Delta\Gamma$ is modelled as $$\Delta\Gamma = aF_1\mu_{a1}e^{-(\tau_\alpha + bv)\delta t} \quad (2)$$

where a and b are constant coefficients, $F_1\mu_{a1}$ is proportional to the first photoacoustic excitation, the exponential decay describes the thermal clearance related to thermal conduction and convection, $\tau_\alpha$ is a time constant related to thermal conduction, $v$ is the flow speed. The second photoacoustic amplitude can be simplified as $$P_2 = \frac{F_2\mu_{a2}}{F_1\mu_{a1}}P_1 + \frac{F_2\mu_{a2}}{F_1\mu_{a1}}P_1^2 A e^{-(\tau_\alpha + bv)\delta t} \quad (3)$$

where $$A = \frac{a}{k\eta\Gamma_0^2}.$$

The coefficients A, $\tau_\alpha$, and b are independent of the blood flow and can be determined via system calibration. In superficial tissue, the ratio of $F_2$ to $F_1$ can be approximated from the tissue surface fluences. To calibrate A, $\tau_\alpha$, and b, the flow speed $v$ and time delays $\delta t$ can be set to different values and then the three coefficients can be fit from the photoacoustic measurements. If a different $\delta t'$ equals to $x\delta t$, other parameters (e.g. surface fluence) remain the same and flow speed is set to zero, then equation (3) can be simplified as $m = Ae^{-\tau_\alpha \delta t}$ and $n = Ae^{-x\tau_\alpha \delta t}$ respectively for time delays $\delta t$ and $\delta t'$. Hence, $$\tau_a = \frac{1}{(1-x)\delta t}\ln\left(\frac{n}{m}\right), A = \left(\frac{n}{m^x}\right)^{\frac{1}{1-x}}.$$

After calibration, the blood flow speed can be determined from the two measured photoacoustic signals using the above.

C. Oxygen Saturation (sO$_2$) Measurement

In one embodiment, oxygen saturation level in the blood can be first determined without considering the increased photoacoustic signal amplitude due to other previous excitations. In such case the sO$_2$ can be determined from the photoacoustic signals at two wavelengths (e.g., 532 nm and 558 nm) as follows $$sO_2 = \frac{\varepsilon_{\lambda_3}^{de} - r\varepsilon_{\lambda_1}^{de}}{\left(\varepsilon_{\lambda_3}^{de} - \varepsilon_{\lambda_3}^{oxy}\right) - r\left(\varepsilon_{\lambda_1}^{de} - \varepsilon_{\lambda_1}^{oxy}\right)} \quad (4)$$

where $$r = \frac{\mu_{a3}}{\mu_{a1}} = \frac{P_3 F_1}{P_1 F_3},$$

$P_{1,3}$ and $F_{1,3}$ are the photoacoustic amplitudes and optical fluences at $\lambda_1 = 532$ nm and $\lambda_3 = 558$ nm, $\varepsilon_{\lambda_{1,3}}^{de}$ and $\varepsilon_{\lambda_{1,3}}^{oxy}$ are the molar extinction coefficients of deoxyhemoglobin (HbR) and oxyhemoglobin (HbO$_2$) at the two wavelengths.

In another embodiment in which three-pulse excitation is applied, the first and second pulses may increase the amplitude of the third photoacoustic signal, leading to an underestimated or otherwise inaccurate sO$_2$. To compensate for this error, the third photoacoustic amplitude is modelled as:

$$P_3 = k\left(\Gamma_0 + aF_1\mu_{a1}e^{-(\tau_\alpha + bv)2\delta t} + aF_2\mu_{a2}e^{-(\tau_\alpha + bv)\delta t}\right)\eta F_3 \mu_{a3} \quad (5)$$

$$= k\Gamma_0 \eta F_3 \mu_{a3} \left(1 + AP_1 e^{-(\tau_\alpha + bv)2\delta t} + AP_1 \frac{F_2 \mu_{a2}}{F_1 \mu_{a1}} e^{-(\tau_\alpha + bv)\delta t}\right)$$

where 2δt is the time delay between the first and third laser pulses, and δt is the time delay between the second and third laser pulses. With the determined flow speed v, a modified r' can be calculated as $$r' = \frac{P_3 F_1}{P_1 F_3} \cdot \frac{1}{1 + AP_1 e^{-(\tau_\alpha + bv)2\delta t} + AP_1 \frac{F_2 \mu_{a2}}{F_1 \mu_{a1}} e^{-(\tau_\alpha + bv)\delta t}} \quad (6)$$

By replacing r in equation (4) with r', the error caused by photoacoustic elevation of the second pulse in sO₂ computation can be compensated for.

Figure 2A:
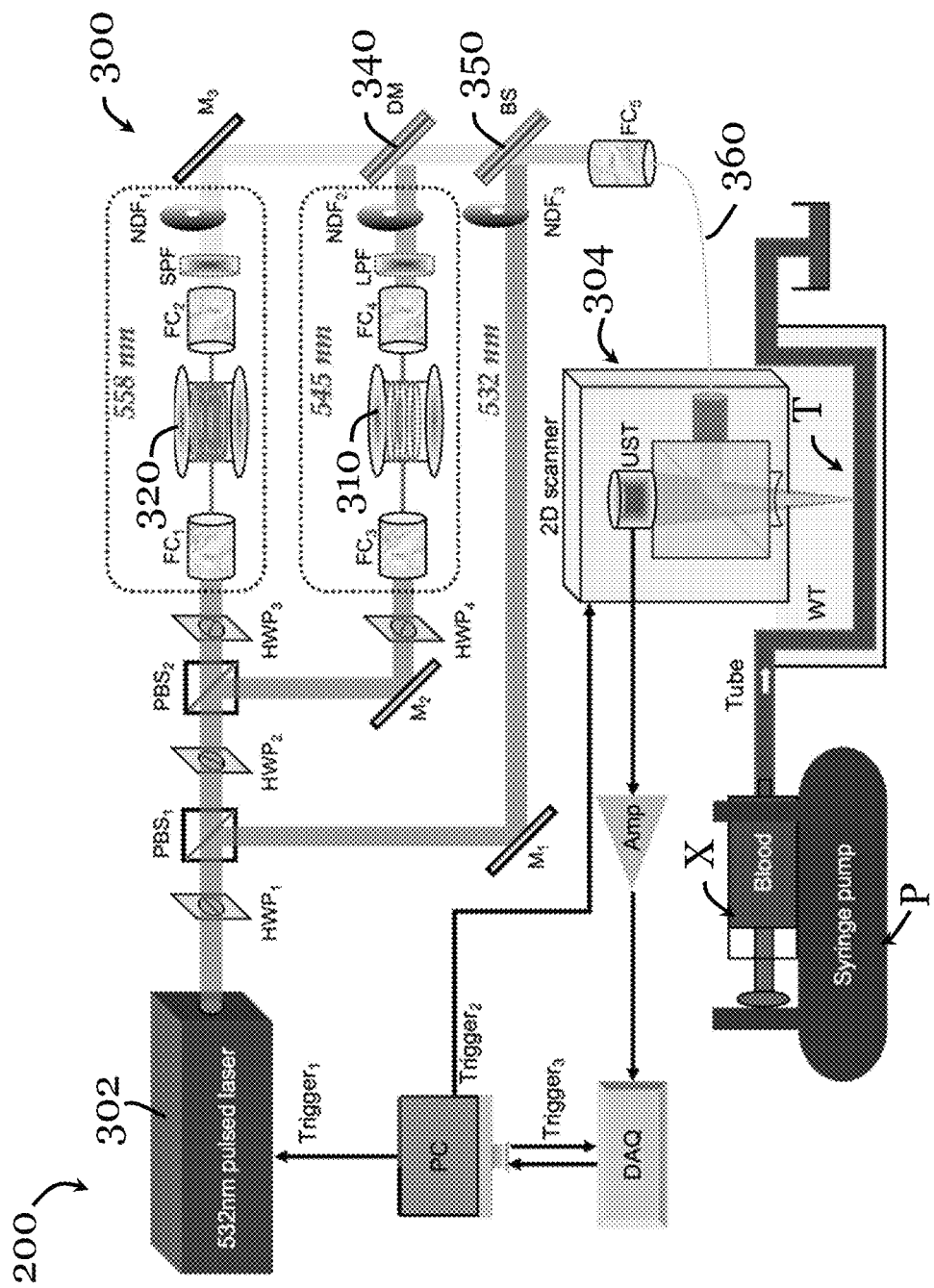
FIG. 2A is a schematic diagram of a system including a photoacoustic imaging or sensing apparatus for performing the method of FIG. 1 in one embodiment of the invention.

FIG. 2A is an imaging system 200 including a photoacoustic imaging or sensing apparatus 300 for performing the method 100 of FIG. 1. The photoacoustic imaging or sensing apparatus 300 can generate three-wavelength laser pulses and the system 200 can accordingly acquire three-wavelength photoacoustic signals in sub-microseconds. The photoacoustic imaging or sensing apparatus 300 may be integrated with the system 300 as a single apparatus. The sample in this example includes a tube T holding a liquid, e.g., blood. The tube T is connected to a syringe X that is in turn connected with a pump P. The tube T is placed in the water tank WT, which can be controlled to be at a substantially constant temperature.

In this embodiment, the photoacoustic imaging or sensing apparatus 300 includes a pulsed laser source 302, an optical processing unit operably connected with the pulsed laser source 302, and a probe 304. The optical processing unit is arranged to receive and process pulsed laser received from the pulsed laser source 302 to provide laser pulses of different wavelengths. The probe 304 connects with the optical processing unit to receive the laser pulses and to transmit them to the sample.

As shown in FIG. 2A, the pulsed laser source 302 is a pump laser, more specifically a nanosecond pulsed laser (532 nm, VPFL-G-20, Spectra-Physics). In this embodiment the pulsed laser source 302 is a single wavelength source. The pulse repetition rate of the pump laser can reach up to 1 MHz and the pulse width is set to 7 ns.

The optical processing unit includes two sets of half-wave plates HWP1 and HWP2 and polarizing beam-splitters PBS1 and PBS2 arranged to separate the pump beam from the source 302 into three optical paths: a 532 nm direct path, a 545 nm Raman path, and a 558 nm Raman path. Note that in the Raman paths, two optical fibers are pumped to generate two new wavelengths, i.e., 545 nm and 558 nm. Each optical path is associated with a respective optical processing sub-unit. The half-wave plates HWP1 and HWP2 (WPH10E-532, Thorlabs Inc) upstream of the polarizing beam-splitters PBS1 and PBS2 are arranged to adjust the power in the optical paths. Optionally, if needed, the fluctuations of the laser pulse energy can be compensated using a photodiode (not shown). The average, standard deviation (SD) and drift of the pulsed light energy for these wavelengths (532 nm, 545 nm, 558 nm) were tested during 66.7 mins. The normalized average and SD for 532 nm, 545 nm, and 558 nm are 33545±24.4, 33887±36.5, and 34522±45.5. And the energy drifts for these 3 wavelengths after 66.7 mins are 8%, 10% and 9%, which are relatively stable.

In the 545 nm Raman path, a 50 m polarization-maintaining single-mode fiber 310 (PM-S405-XP, NUFERN) is used to generate the 545 nm pulse through stimulated-Raman-scattering effect and to delay the pulse by 260 ns (as measured by a photodiode (not shown). The theoretical time delay in a 50 m fiber is ~243 ns but due to the time delay in free space the actual time delay in this example is increased. By adjusting the incident pulse energy and polarization state, the 50 m fiber 310 can maximize the pulse energy of the 545 nm and avoids generating other stokes wavelengths. In this embodiment, the energy and polarization are adjusted to generate only the first wavelength (545 nm) but not other higher order Stokes wavelengths. The beam combination is for 532 nm and 545 nm. A long-pass filter LPF (T540lpxr, CHROMA) is placed after the 50 m Raman fiber to pass the 545 nm and reflect the 532 nm. Respective fiber couplers FC3 and FC4 are placed upstream and downstream of the single-mode fiber 310. For system calibration, another 30 m polarization-maintaining single-mode fiber (not shown) is used to generate and delay the 545 nm by 163 ns.

In the 558 nm Raman path, the pump beam is coupled into a loom graded-index multi-mode fiber 320 (GIMMSC(50/125)HT, FIBERCORE) to generate 558 nm laser pulse with a 512 ns time delay. Because the stimulated-Raman-scattering threshold of a single-mode fiber is limited to its length, the highest 558 nm pulse energy generated by a loom single-mode fiber may not be enough for sensitive photoacoustic imaging or sensing in some applications, thus this path uses a multi-mode fiber 320 not a single-mode fiber. A long fiber is easier to generate Stokes wavelength via stimulated-Raman-scattering and makes the Raman threshold lower. In this embodiment a loom graded-index multi-mode fiber 320 is used to increase the stimulated-Raman-scattering threshold. Although the loom stimulated-Raman-scattering fiber 320 is multi-mode for the pump light, the generated 558 nm is nearly single mode due to the Raman beam clean-up effect. A half-wave plate HWP3 adjusts the polarization of the incident light to maximize the 558 nm energy. A short pass filter SPF (RPE570SP, OMEGA) downstream of the loom fiber 320 is arranged to reject wavelengths longer than 570 nm. Respective fiber couplers FC1 and FC2 are placed upstream and downstream of the multi-mode fiber 320.

A 550 nm long-pass dichroic mirror 340 (T550lpxr-UF1, CHROMA) is used to combine the 545 nm and 558 nms. A beam splitter, e.g., a 10/90 beam splitter 350, combines the direct 532 nm with the delayed 545 nm and 558 nm. A variable neutral density filter NDF1, NDF2, NDF3 (NDC-50C-2, Thorlabs Inc) is added to each respective path to adjust the output energy. Finally, the three wavelengths are coupled into an OR-PAM probe 304 via a fiber coupler FC5 and 2 m single-mode fiber 360 (P1-460B-FC-2, Thorlabs Inc).

In this example, the fiber coupling efficiencies for all the single-mode beams are higher than 50%. When coupling the 558 nm beam to the 2 m single-mode fiber, because the 558 nm is not 100% single mode, the coupling efficiency is ~30%. The pulse energy on the sample surface for each wavelength is higher than 100 nJ.

In the probe 304, the laser beam from the 2 m fiber 360 is focused by a pair of achromatic doublets (AC064-013-A, Thorlabs). The focused optical beam is reflected on an optical/acoustic beam combiner, transmits through a plano-concave lens (45-697, Edmund optics), then illuminates the sample S. Induced ultrasonic waves (photoacoustic signals generated by the sample in response to the laser pulses) are collimated by the plano-concave lens, transmits through the optical/acoustic beam combiner, and detected by a 50-MHz broadband piezoelectric transducer (V214-BC-RM, Olympus). The focused optical beam is coaxially and confocally aligned with the focused ultrasonic detection beam to optimize the detection sensitivity.

At each pump laser pulse, the laser apparatus 300 generates three temporally separated laser pulses at 532 nm, 545 nm, and 558 nm, and the system 200 sequentially acquires three depth-resolved A-lines at the three wavelengths. Volumetric photoacoustic images are acquired by raster scanning the photoacoustic probe in the lateral plane. The lateral resolution is 3.4 μm. The time to acquire one set of three-wavelength photoacoustic signals is ~500 ns. If the mechanical scanning or blood flow speed is less than 1 cm/s, the misalignment among the three A-lines would be smaller than 5 nm, which is negligible compared with the lateral resolution. Other details of the system 200 including the amplifier ("Amp"), the data acquisition module ("DAQ"), and the processor ("PC") are omitted for simplicity. Briefly, the amplifier is arranged to amplify the received photoacoustic signals; the data acquisition module is arranged to regulate the received amplified photoacoustic signals; and the processor is arranged to control operation of the system 200, including providing trigger pulse to operate the source 302, providing trigger pulse to operate the probe 304, providing trigger pulse to operate the data acquisition module, etc. The processor may also be used to process the photoacoustic signals to determine the one or more parameters associated with the sample, such as those parameters discussed above with respect to FIG. 1.

Figure 2B:
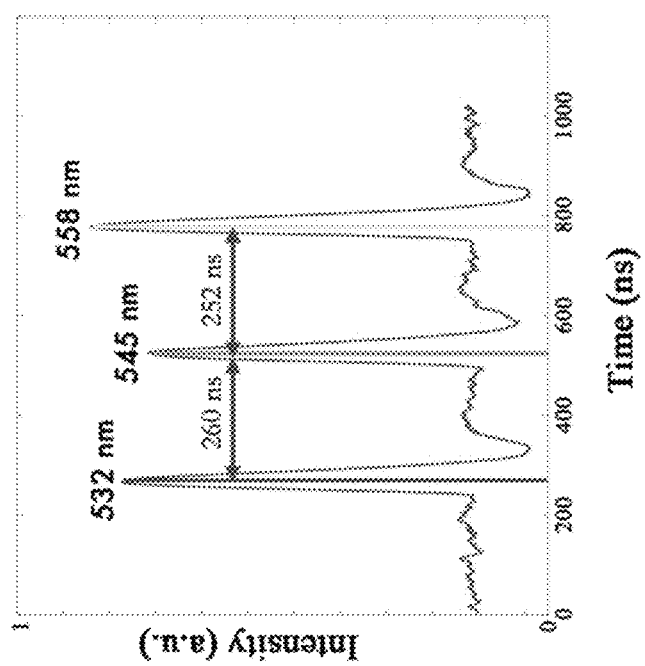
FIG. 2B is a graph showing time differences between different laser pulses provided by the system of FIG. 2A in one embodiment of the invention.

FIG. 2B is a graph showing the time differences between different laser pulses provided by the system 200 of FIG. 2A.

To validate the exponential model in equation (3), an experiment was performed to measure the decay constants at different blood flow speeds ranging from 0 to 23 mm/s in a blood phantom as a sample in the system of FIG. 2A. The phantom is anticoagulated bovine blood filled in transparent rubber tube (0.25 mm inner diameter, TYGON S-54-HL, Norton Performance Plastics, N.J.). The blood flow speed is set by a syringe pump. The photoacoustic probe and the blood sample are immersed in a water tank for acoustic coupling. The laser repetition rate is 4 kHz. The pulse energy on the sample surface is 100 nJ for each wavelength. The exponential decay model is fitted with the least square criteria. The exponential decay constants at different set flow speeds are plotted in FIG. 3A. As expected, the decay constant is a linear function of the flow speed with a determination coefficient ($R^2$) of 0.952, indicating the high dependence of the increased photoacoustic amplitude on the flow speed. A, $\tau_\alpha$, and b are fitted as 0.11±0.01 (SD), 10.19±0.85 (SD) and 0.30±0.04 (SD). With the fitted coefficients, the flow speed can be determined from two photoacoustic signals. Using the same experimental setup, the flow speed measurement was validated in blood phantom. As shown in FIG. 3B, the measured flow speed is averaged by 100 times and compared with the set flow speed. The measured flow speed is proportional to the set flow speed, showing that the dual-pulse approach is applicable for measuring the blood flow speed.

Figure 4E:
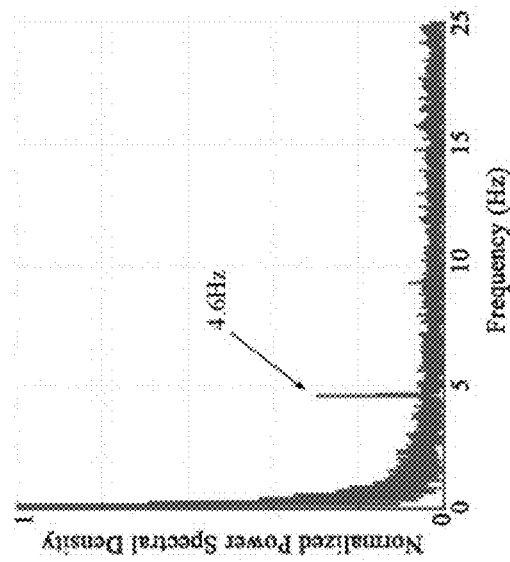
FIG. 4E is a graph showing the linear relationship between the results obtained in FIGS. 4C and 4D.
Figure 4F:
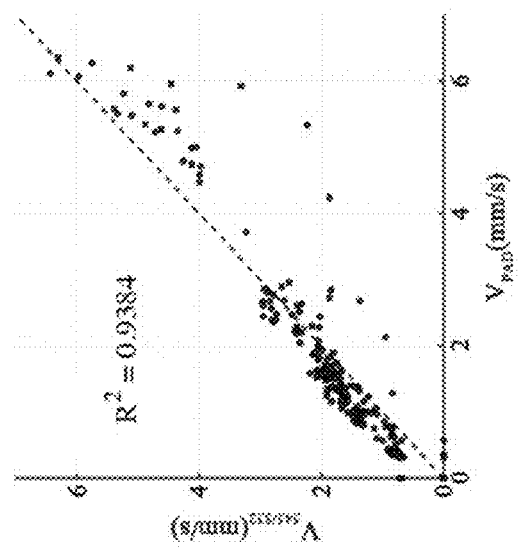
FIG. 4F is a graph showing a frequency spectrum of the dual-pulse flow speed in the artery as labelled with a black star in FIG. 4A.
Figure 4G:
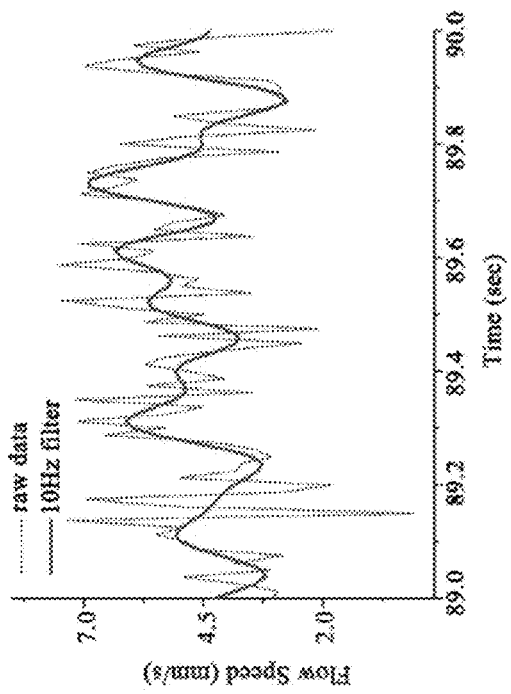
FIG. 4G is a graph showing the temporal variation of blood flow speed in the artery at different times (averaged by 100 times), along with a low-pass filtered curve cut-off at 10 Hz.

Dual-pulse flowmetry in the above embodiment was used to measure blood flow speed in the mouse ear. FIGS. 4A to 4G show the related results. Specifically, FIG. 4A shows photoacoustic imaging or sensing of blood vessels in the mouse ear acquired with 532 nm wavelength; FIG. 4B shows flow speed image measured by dual-pulse flowmetry in the above embodiment. FIGS. 4C and 4D are flow speed profiles along with the dashed line 410 in FIG. 4A measured by the existing photoacoustic Doppler method and the dual-pulse method. Details of the existing photoacoustic Doppler method can be found in H. Fang, K. Maslov, L. V Wang, *photoacoustic Doppler flow measurement in optically scattering media*, Appl. Phys. Lett. 91 (2007) 264103, J. Brunker, P. Beard, *Velocity measurements in whole blood using acoustic resolution photoacoustic Doppler*, Biomed. Opt. Express. 7 (2016) 2789-2806, R. Zhang, J. Yao, K. I. Maslov, L. V Wang, *Structured-illumination photoacoustic Doppler flowmetry of axial flow in homogeneous scattering media*, Appl. Phys. Lett. 103 (2013) 94101, J. Yao, L. V Wang, *Transverse flow imaging based on photoacoustic Doppler bandwidth broadening*, J. Biomed. Opt. 15 (2010) 021304, and J. Yao, K. I. Maslov, Y. Shi, L. A. Taber, L. V Wang, *In vivo photoacoustic imaging of transverse blood flow by using Doppler broadening of bandwidth*, Opt. Lett. 35 (2010) 1419-1421. FIG. 4E illustrates the linear relationship between the photoacoustic Doppler results and the dual-pulse results. A linear fitting gives the $R^2$ of 0.9384. $V_{PAD}$ is the flow speed measured by photoacoustic Doppler method. $V_{545/532}$ is the flow speed measured by the dual-pulse method. FIG. 4F shows the spectrum of the dual-pulse flow speed in the artery as labeled with a star 420 in FIG. 4A. A heartbeat rate of 4.6 Hz is observed. FIG. 4G shows the time-domain blood flow speed in the artery which is averaged by 100 times. The thicker line is a lowpass filtered result cut off at 10 Hz.

The in vivo experiment to obtain FIGS. 4A to 4G was carried out on anaesthetized female BALB/c mice (4 weeks). The region of interest (ROI) shown in FIG. 4A is 0.5 mm×0.5 mm. The raster scanning takes 40 seconds with a 10-Hz b-scan rate. The laser repetition rate is 4 kHz and the pulse energy for each wavelength is ~80 nJ. Using the fitted model, the blood flow speed in the ROI is calculated at each pixel from the photoacoustic signals at 545 nm and 532 nm as shown in FIG. 4B. In the artery, the averaged flow speed is ~6 mm/s. In the vein, the averaged flow speed is ~3 mm/s.

For comparison, both photoacoustic Doppler (PAD) flowmetry and dual-pulse flowmetry are used to measure the same blood flow speed in the mouse ear. Because PAD needs to use multiple A-lines to calculate flow speed, the scanning mode is changed to acquiring multiple successive A-lines at each point. The photoacoustic probe was scanned along a dashed line 410 in FIG. 4A and the flow speed profile was measured using the two methods (existing photoacoustic Doppler method and the dual-pulse method of the present embodiment). 200 successive A-lines at each point were used to do autocorrelation for PAD calculation. In the dual-pulse method of the present embodiment, each pair of 545 nm and 532 nm photoacoustic data can be used to calculate flow speed. For comparison, the dual-pulse flow result was averaged over all A-line pairs. Flow results calculated by the two methods are shown in FIGS. 4C and 4D. The two results were compared by fitting them to a linear regression model, as shown in FIG. 4E. The determination coefficient $R^2$ is 0.938, indicating that the flow results measured by the two methods match well.

To further demonstrate the high speed of dual-pulse flowmetry, the mouse heartbeat in the artery was measured. The measurement spot is labeled with a star 420 in FIG. 4A. The maximum amplitudes of multiple successive A-lines was calculated and the blood flow speeds were determined using equation (3). Fourier transformation was applied to the blood flow speeds at multiple A-lines. The frequency spectrum shows a peak at ~4.6 Hz in FIG. 4F, which matches with the heartbeat rate of the mouse under anesthesia. The heart beating can also be visible in the time domain as shown in FIG. 4G. The data was averaged 100 times and then filtered with a 10-Hz lowpass filter. The heartbeat cycles become obvious in the measured blood flow speeds. This result shows the dual-pulse method is advantageous in A-line based flow imaging.

Figure 6E:
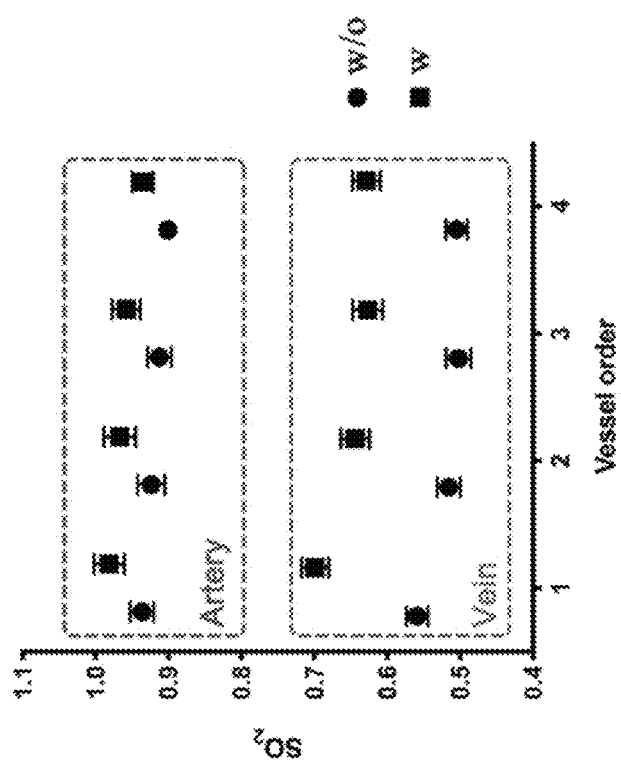
FIG. 6E is a plot showing comparison of oxygen saturation measurement without and with compensation in selected artery-vein pairs labelled by the lines in FIG. 5B.

Using the three-wavelength system 200 of FIG. 2A, the present invention can be used to simultaneously quantify hemoglobin concentration, blood flow speed, and oxygen saturation in vivo. One laser pulse may increase the photoacoustic amplitude generated by the following laser pulses (e.g., because an earlier laser pulse may increase the photoacoustic excitation efficiency F of a subsequent laser pulse). This may cause a systematic error in $sO_2$ calculation. With system calibration, it has been shown above that the error can be compensated for in the $sO_2$ imaging. In vivo $sO_2$ comparison results are shown in FIGS. 5A to 6E. The laser repetition rate is 4 kHz. Pulsed energy for each wavelength is ~80 nJ. The imaging area is 8.75 mm×10 mm. FIG. 5A shows the normalized hemoglobin concentration imaged at 532 nm. The system has enough SNR (>20 dB) to show the capillaries. The blood flow speed calculated by the dual-pulse method is shown in FIG. 5B. Four artery-vein pairs of vessels labelled with the lines are selected to plot profiles of the blood flow speed, as shown in FIGS. 6A to 6D. From the root to the tip of the ear, the blood flow speed in the artery decreases from ~7 mm/s to ~3.3 mm/s, and in the vein, the flow speed maintains ~2 mm/s. $sO_2$ images without and with compensation are shown in FIGS. 4C and 4D. Artery-vein pairs labeled with the lines are selected to compare the $sO_2$ values. As shown in FIG. 6E, without compensation, the artery $sO_2$ values at the first to the fourth spots are 0.94±0.01 (SE), 0.92±0.02 (SE), 0.91±0.02 (SE) and 0.90±0.02 (SE), and the vein $sO_2$ values at the same spots are 0.56±0.01 (SE), 0.52±0.02 (SE), 0.50±0.02 (SE), 0.50±0.01 (SE). With compensation, the artery $sO_2$ values increase to 0.98±0.02 (SE), 0.96±0.02 (SE), 0.95±0.02 (SE), 0.94±0.01 (SE), and the vein $sO_2$ values become 0.69±0.02 (SE), 0.64±0.02 (SE), 0.63±0.02 (SE), 0.63±0.01 (SE).

Figure 7:
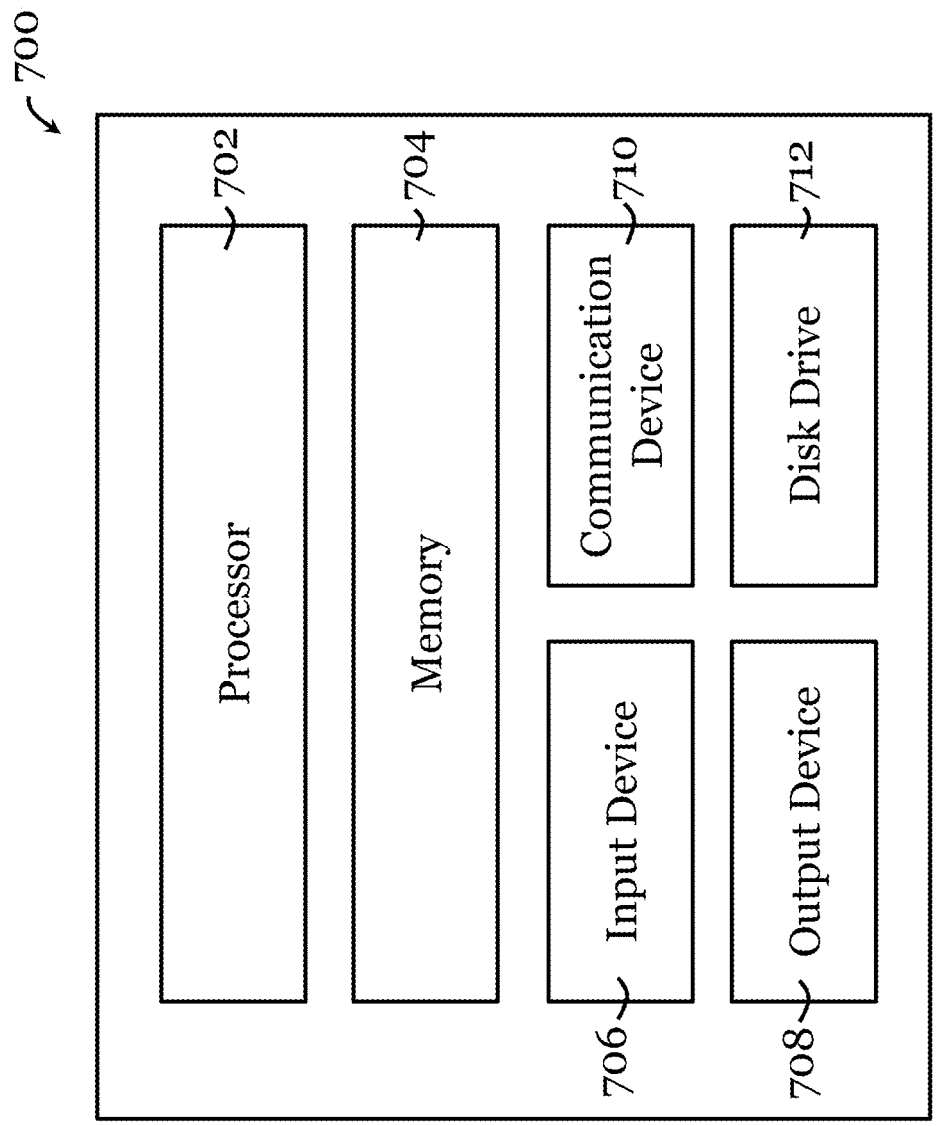
FIG. 7 is a block diagram of an information handling system arranged to perform the method of FIG. 1 in one embodiment of the invention.

Referring to FIG. 7, there is shown a schematic diagram of an exemplary information handling system 700 that can be used as a computer, computing device, information processing system, or the like, to perform the method of any of the above embodiments. The information handling system 700 can be used in the determination of hemoglobin concentration, flow, and oxygen saturation, by processing the photoacoustic signals with the respective models. The information handling system 700 may be partly or completely integrated with the system 200 of FIG. 2 or the photoacoustic imaging or sensing apparatus 300 of FIG. 2. The information handling system 700 may alternately be an information handling system separate from the system 200 or the photoacoustic imaging or sensing apparatus 300.

The information handling system 700 may have different configurations, and it generally comprises suitable components necessary to receive, store, and execute appropriate computer instructions, commands, or codes. The main components of the information handling system 700 are a processor 702 and a memory unit 704. The processor 702 may be formed by one or more of: CPU, MCU, controllers, logic circuits, Raspberry Pi chip, digital signal processor (DSP), application-specific integrated circuit (ASIC), Field-Programmable Gate Array (FPGA), or any other digital or analog circuitry configured to interpret and/or to execute program instructions and/or to process data. The memory unit 704 may include one or more volatile memory unit (such as RAM, DRAM, SRAM), one or more non-volatile unit (such as ROM, PROM, EPROM, EEPROM, FRAM, MRAM, FLASH, SSD, NAND, and NVDIMM), or any of their combinations. Preferably, the information handling system 700 further includes one or more input devices 706 such as a keyboard, a mouse, a stylus, an image scanner, a microphone, a tactile input device (e.g., touch sensitive screen), and an image/video input device (e.g., camera). The information handling system 700 may further include one or more output devices 708 such as one or more displays (e.g., monitor), speakers, disk drives, headphones, earphones, printers, 3D printers, etc. The display may include a LCD display, a LED/OLED display, or any other suitable display that may or may not be touch sensitive. The information handling system 700 may further include one or more disk drives 712 which may encompass solid state drives, hard disk drives, optical drives, flash drives, and/or magnetic tape drives. A suitable operating system may be installed in the information handling system 700, e.g., on the disk drive 712 or in the memory unit 704. The memory unit 704 and the disk drive 712 may be operated by the processor 702. The information handling system 700 also preferably includes a communication device 710 for establishing one or more communication links (not shown) with one or more other computing devices such as servers, personal computers, terminals, tablets, phones, or other wireless or handheld computing devices. The communication device 710 may be a modem, a Network Interface Card (NIC), an integrated network interface, a radio frequency transceiver, an optical port, an infrared port, a USB connection, or other wired or wireless communication interfaces. The communication links may be wired or wireless for communicating commands, instructions, information and/or data. Preferably, the processor 702, the memory unit 704, and optionally the input devices 706, the output devices 708, the communication device 710 and the disk drives 712 are connected with each other through a bus, a Peripheral Component Interconnect (PCI) such as PCI Express, a Universal Serial Bus (USB), an optical bus, or other like bus structure. In one embodiment, some of these components may be connected through a network such as the Internet or a cloud computing network. A person skilled in the art would appreciate that the information handling system 700 shown in FIG. 7 is merely exemplary and different information handling systems 700 with different configurations may be applicable in the invention.

Although not required, the embodiments described with reference to the Figures can be implemented as an application programming interface (API) or as a series of libraries for use by a developer or can be included within another software application, such as a terminal or personal computer operating system or a portable computing device operating system. Generally, as program modules include routines, programs, objects, components and data files assisting in the performance of particular functions, the skilled person will understand that the functionality of the software application may be distributed across a number of routines, objects or components to achieve the same functionality desired herein.

It will also be appreciated that where the methods and systems of the invention are either wholly implemented by computing system or partly implemented by computing systems then any appropriate computing system architecture may be utilized. This will include stand-alone computers, network computers, dedicated or non-dedicated hardware devices. Where the terms "computing system" and "computing device" are used, these terms are intended to include any appropriate arrangement of computer or information processing hardware capable of implementing the function described.

The above embodiments of the invention can simultaneously image hemoglobin concentration, blood flow speed, and oxygen saturation within sub-microseconds, using limited number of lase pulses. A dual-pulse approach can be used to measure the blood flow with only two short-delayed A-lines. A dual-pulse (or multiple-pulse) flowmetry can be performed based on a series of A-lines. The principle originates from the first laser pulse's heating effect on the second, subsequent pulse, which can be affected by the flow speed. An exponential model can be used to quantify the blood flow speed from two photoacoustic measurements. Based on the exponential model, the error in $sO_2$ quantification can also be compensated for. Simultaneous multi-parameter imaging can be achieved. Dual-pulse flowmetry of the above embodiments can accurately, quickly, and efficiently measure blood flow speed. It requires only two photoacoustic measurements in sub-microseconds. Unlike conventional functional OR-PAM, the dual-pulse flowmetry and three-wavelength OR-PAM do not need multiple repeated A-line imaging at one spot, which saves imaging time, increases throughput, and may mitigate potential motion artifacts. This technical advance enables dynamic functional imaging at the sub-microseconds scale.

Compared with the existing systems and methods, the system(s) and method(s) in the above embodiments include one or more of the following advantages:
1. Conventional flowmetry measurement is at dozens of millisecond scale; the flow measurement method/system of the above embodiment(s) is at sub-microsecond scale, which can realize the real-time flowmetry measurement considering the normal blood flow speed is at several millisecond scale.
2. Conventional method/system calculates the flow speed from hundreds of measurements; the flow measurement method/system of the above embodiment(s) can obtain flow speed from a single-shot.
3. Conventional method/system can hardly simultaneously measure multiple physiological parameters, in particular hemoglobin concentration, oxygen saturation, and blood flow; the method/system of the above embodiment(s) can simultaneous imaging of multiple physiological parameters, in particular hemoglobin concentration, oxygen saturation, and blood flow with a single raster scan.
4. Conventional multi-wavelength method/system requires more than one laser to generate multiple wavelengths; the method/system of the above embodiment(s) can generate multiple wavelengths based on single laser.

In other systems and methods embodiments, one or more alternative or further advantages may be provided.

It will be appreciated by persons skilled in the art that numerous variations and/or modifications may be made to the invention as shown in the specific embodiments without departing from the invention as broadly described. The described embodiments of the invention should therefore be considered in all respects as illustrative, not restrictive. For example, the method/system in the above embodiments can be applied not only in vivo, but also in vitro. The method/system need not be used to measure properties of human or animals, but can be any other objects, devices, apparatus, etc. Various features indicated as optional (using "may be", "e.g.,", or the like) can be replaced with other alternatives. Various parameters or constants can be set differently, dependent on applications. For example, the wavelengths of the laser pulses can be different from those illustrated; the time delay between the laser pulses can be set differently, etc.

The invention claimed is:

1. A method for determining flow speed based on photoacoustic imaging or sensing, comprising:
   receiving a first photoacoustic signal and a second photoacoustic signal from a sample in response to transmission of a first laser pulse and a second laser pulse to the sample, the first laser pulse has a first wavelength and the second laser pulse has a second wavelength different from the first wavelength; and
   processing the first photoacoustic signal and the second photoacoustic signal based on a flow model that relates photoacoustic signals with flow speed to determine a flow speed of a liquid flow in the sample;
   wherein the processing includes:
      determining a first amplitude of the first photoacoustic signal and a second amplitude of the second photoacoustic signal, and
      applying the first and second amplitudes to the flow model;
   wherein the flow model is an exponential decay model and relates the first and second amplitudes with flow speed by:

$$P_2 = \frac{F_2 \mu_{a2}}{F_1 \mu_{a1}} P_1 + \frac{F_2 \mu_{a2}}{F_1 \mu_{a1}} P_1^2 A e^{-(\tau_\alpha + bv)\delta t}$$

where $P_1$ is the first amplitude, $P_2$ is the second amplitude, $F_1$ and $F_2$ are optical fluences associated with the first and second laser pulses, $\mu_{a1}$ and $\mu_{a2}$ are optical absorption coefficients associated with the first and second laser pulses, $A$, $\tau_\alpha$, and $b$ are coefficients independent of the flow, $\delta t$ is a time delay between the first and second laser pulses, $v$ is the flow speed.

2. The method of claim 1, further comprising:
   transmitting the first laser pulse and the second laser pulse to the sample;
   wherein the first laser pulse and the second laser pulse are provided by an optical processing unit operably connected with a single pulsed laser source.

3. The method of claim 2, wherein a time difference between transmission of the first and second laser pulses is in the order of micro-seconds or nano-seconds.

4. The method of claim 1, wherein a time difference between transmission of the first and second laser pulses is in the order of micro-seconds or nano-seconds.

5. The method of claim 1, wherein the first wavelength of the first laser pulse and the second wavelength of the second laser pulse are isosbestic wavelengths.

6. The method of claim 1, further comprising:
   processing one of the first photoacoustic signal and the second photoacoustic signal based on a photoacoustic absorption model to determine particulate concentration in the liquid.

7. The method of claim 1, wherein the sample is a human or animal, and wherein the method is performed in vivo.

8. The method of claim 7, wherein the liquid is blood.

9. The method of claim 8, further comprising:
   processing one of the first photoacoustic signal and the second photoacoustic signal based on a photoacoustic absorption model to determine hemoglobin concentration in the blood.

10. The method of claim 8, further comprising:
receiving a third photoacoustic signal from the sample in response to transmission of a third laser pulse to the sample, the third laser pulse has a third wavelength different from the first wavelength and the second wavelength; and
processing at least one of the first photoacoustic signal and the second photoacoustic signal, and the third photoacoustic signal, based on a linear spectral unmixing model to determine oxygen saturation in the blood.

11. The method of claim 10, wherein the first, second, and third laser pulses are transmitted sequentially, wherein a time difference between transmission of the first and second laser pulses is in the order of micro-seconds, and a time difference between transmission of the second and third laser pulses is in the order of micro-seconds;
wherein the first, second, and third laser pulses are provided by an optical processing unit operably connected with a single pulsed laser source.

12. The method of claim 10, wherein the first, second, and third laser pulses are transmitted sequentially, wherein a time difference between transmission of the first and second laser pulses is in the order of nano-seconds, and a time difference between transmission of the second and third laser pulses is in the order of nano-seconds;
wherein the first, second, and third laser pulses are provided by an optical processing unit operably connected with a single pulsed laser source.

13. The method of claim 10, wherein the processing includes
determining at least a first amplitude of the first photoacoustic signal and a third amplitude of the third photoacoustic signal; and
applying at least the first and third amplitudes to the linear spectral unmixing model.

14. The method of claim 13, wherein the linear spectral unmixing model is represented by:

$$sO_2 = \frac{\varepsilon_{\lambda_3}^{de} - r\varepsilon_{\lambda_1}^{de}}{\left(\varepsilon_{\lambda_3}^{de} - \varepsilon_{\lambda_3}^{oxy}\right) - r\left(\varepsilon_{\lambda_1}^{de} - \varepsilon_{\lambda_1}^{oxy}\right)}$$

where $sO_2$ is the oxygen saturation in the blood, $$r = \frac{\mu_{a3}}{\mu_{a1}} = \frac{P_3 F_1}{P_1 F_3},$$

$P_1$ and $P_3$ are the first and third amplitudes, $F_1$ and $F_3$ are optical fluences associated with the first and third laser pulses, $\varepsilon_{\lambda_{1,3}}^{de}$ and $\varepsilon_{\lambda_{1,3}}^{oxy}$ are molar extinction coefficients of oxyhemoglobin and deoxyhemoglobin at the first and third wavelengths.

15. The method of claim 13, wherein the linear spectral unmixing model is a model that relates photoacoustic signals with oxygen saturation.

16. The method of claim 15, wherein the linear spectral unmixing model is represented by:

$$sO_2 = \frac{\varepsilon_{\lambda_3}^{de} - r'\varepsilon_{\lambda_1}^{de}}{\left(\varepsilon_{\lambda_3}^{de} - \varepsilon_{\lambda_3}^{oxy}\right) - r'\left(\varepsilon_{\lambda_1}^{de} - \varepsilon_{\lambda_1}^{oxy}\right)}$$

where $sO_2$ is the oxygen saturation in the blood, $$r' = \frac{P_3 F_1}{P_1 F_3} \cdot \frac{1}{1 + AP_1 e^{-(\tau_\alpha + bv)2\delta t} + AP_1 \frac{F_2 \mu_{a2}}{F_1 \mu_{a1}} e^{-(\tau_\alpha + bv)\delta t}},$$

$P_1$, $P_2$ and $P_3$ are the first, second, and third amplitudes, $F_1$, $F_2$, and $F_3$ are optical fluences associated with the first, second, and third laser pulses, $\delta t$ is a time delay between the first and second laser pulses, as well as a time delay between the second and third laser pulses, A, $\tau_\alpha$, and b are coefficients independent of the flow, $\mu_{a1}$ and $\mu_{a2}$ are optical absorption coefficients associated with the first and second laser pulses, $\varepsilon_{\lambda_{1,3}}^{de}$ and $\varepsilon_{\lambda_{1,3}}^{oxy}$ are molar extinction coefficients of oxyhemoglobin and deoxyhemoglobin at the first and third wavelengths.

17. A system for determining flow speed based on photoacoustic imaging or sensing, comprising:
one or more processors arranged to:
receive a first photoacoustic signal and a second photoacoustic signal from a sample in response to transmission of a first laser pulse and a second laser pulse to the sample, the first laser pulse has a first wavelength and the second laser pulse has a second wavelength different from the first wavelength; and
process the first photoacoustic signal and the second photoacoustic signal based on a flow model that relates photoacoustic signals with flow speed to determine a flow speed of a liquid flow in the sample;
wherein the one or more processors are arranged to perform the processing by, at least:
determining a first amplitude of the first photoacoustic signal and a second amplitude of the second photoacoustic signal, and
applying the first and second amplitudes to the flow model;
wherein the flow model is an exponential decay model and relates the first and second amplitudes with flow speed by:

$$P_2 = \frac{F_2 \mu_{a2}}{F_1 \mu_{a1}} P_1 + \frac{F_2 \mu_{a2}}{F_1 \mu_{a1}} P_1^2 A e^{-(\tau_\alpha + bv)\delta t}$$

where $P_1$ is the first amplitude, $P_2$ is the second amplitude, $F_1$ and $F_2$ are optical fluences associated with the first and second laser pulses, $\mu_{a1}$ and $\mu_{a2}$ are optical absorption coefficients associated with the first and second laser pulses, A, $\tau_\alpha$, and b are coefficients independent of the flow, $\delta t$ is a time delay between the first and second laser pulses, $v$ is the flow speed.

18. The system of claim 17, further comprising a photoacoustic imaging or sensing apparatus having a probe arranged to transmit the first laser pulse and the second laser pulse to the sample.

19. The system of claim 17, wherein the one or more processors are arranged to process one of the first photoacoustic signal and the second photoacoustic signal based on a photoacoustic absorption model to determine particulate concentration in the liquid.

20. The system of claim 17, wherein the sample is a human or animal, and wherein the liquid is blood.

21. The system of claim 20, wherein the one or more processors are arranged to process one of the first photoacoustic signal and the second photoacoustic signal based on a photoacoustic absorption model to determine hemoglobin concentration in the blood.

22. The system of claim 20, wherein the one or more processors are further arranged to
receive a third photoacoustic signal from the sample in response to transmission of a third laser pulse to the sample, the third laser pulse has a third wavelength different from the first wavelength and the second wavelength; and
process at least one of the first photoacoustic signal and the second photoacoustic signal, and the third photoacoustic signal, based on a linear spectral unmixing model to determine oxygen saturation in the blood.

23. The system of claim 22, further comprising a photoacoustic imaging or sensing apparatus having a probe, and wherein the probe of the photoacoustic imaging or sensing apparatus is arranged to transmit the first, second, and third laser pulses sequentially, wherein a time difference between transmission of the first and second laser pulses is in the order of micro-seconds or nano-seconds, and a time difference between transmission of the second and third laser pulses is in the order of micro-seconds or nano-seconds.

24. The system of claim 22, wherein the one or more processors are further arranged to
determine at least a first amplitude of the first photoacoustic signal and a third amplitude of the third photoacoustic signal; and
apply at least the first and third amplitudes to the linear spectral unmixing model.

25. The system of claim 24, wherein the linear spectral unmixing model is represented by:

$$sO_2 = \frac{\varepsilon_{\lambda_3}^{de} - r'\varepsilon_{\lambda_1}^{de}}{\left(\varepsilon_{\lambda_3}^{de} - \varepsilon_{\lambda_3}^{oxy}\right) - r'\left(\varepsilon_{\lambda_1}^{de} - \varepsilon_{\lambda_1}^{oxy}\right)}$$

where $sO_2$ is the oxygen saturation in the blood, $$r' = \frac{P_3 F_1}{P_1 F_3} \cdot \frac{1}{1 + AP_1 e^{-(\tau_\alpha + bv)2\delta t} + AP_1 \frac{F_2 \mu_{a2}}{F_1 \mu_{a1}} e^{-(\tau_\alpha + bv)\delta t}},$$

$P_1$, $P_2$ and $P_3$ are the first, second, and third amplitudes, $F_1$, $F_2$, and $F_3$ are optical fluences associated with the first, second, and third laser pulses, $\delta t$ is a time delay between the first and second laser pulses, as well as a time delay between the second and third laser pulses, A, $\tau_\alpha$, and b are coefficients independent of the flow, $\mu_{a1}$ and $\mu_{a2}$ are optical absorption coefficients associated with the first and second laser pulses, $\varepsilon_{\lambda_{1,3}}^{de}$ and $\varepsilon_{\lambda_{1,3}}^{oxy}$ are molar extinction coefficients of oxyhemoglobin and deoxyhemoglobin at the first and third wavelengths.

26. The system of claim 17, further comprising a photoacoustic imaging or sensing apparatus comprising:
a pulsed laser source;
an optical processing unit operably connected with the pulsed laser source, the optical processing unit being arranged to process pulsed laser received from the pulsed laser source to provide laser pulses of different wavelengths; and
a probe operably connected with the optical processing unit, for transmitting the laser pulses to the sample;
wherein the photoacoustic imaging or sensing apparatus comprises at least part of the one or more processors.

27. The system of claim 26, wherein the pulsed laser source is arranged to provide laser pulses of the first wavelength.

28. The system of claim 26, wherein the laser pulses of different wavelengths are temporally separated laser pulses.

29. The system of claim 28, wherein the optical processing unit includes:
a first optical processing sub-unit arranged in a first optical path, arranged to provide a pulse laser of the first wavelength;
a second optical processing sub-unit arranged in a second optical path arranged to provide a pulse laser of the second wavelength different from the first wavelength; and
a third optical processing sub-unit arranged in a third optical path arranged to provide a pulse laser of a third wavelength different from the first and second wavelengths.

30. The system of claim 29, wherein the first optical processing sub-unit includes a power adjuster arranged to adjust a power of the laser pulse provided by the pulsed laser source.

31. The system of claim 30, wherein the second optical processing sub-unit includes an optical regulator arranged to alter a wavelength of the laser pulse provided by the pulsed laser source by excitation based on stimulated Raman scattering and to introduce a time delay to the laser pulse provided by the pulsed laser source.

32. The system of claim 31, wherein the optical regulator comprises a single-mode optical fiber.

33. The system of claim 31, wherein the third optical processing sub-unit includes an optical regulator arranged to alter a wavelength of the laser pulse provided by the pulsed laser source by excitation based on stimulated Raman scattering and to introduce a time delay to the laser pulse provided by the pulsed laser source.

34. The system of claim 33, wherein the optical regulator comprises a multi-mode optical fiber.

35. A method for determining oxygen saturation in blood of human or animal in vivo based on photoacoustic imaging or sensing, comprising:
receiving a first photoacoustic signal, a second photoacoustic signal, and a third photoacoustic signal from a human or animal in response to transmission of a first laser pulse, a second laser pulse, and a third laser pulse to the human or animal, the first laser pulse has a first wavelength, the second laser pulse has a second wavelength different from the first wavelength, the third laser pulse has a third wavelength different from the first wavelength and the second wavelength; and
processing at least the first photoacoustic signal and the third photoacoustic signal based on a linear spectral unmixing model to determine oxygen saturation in blood of the human or animal;
wherein the processing includes:
determining at least an amplitude of the first photoacoustic signal and an amplitude of the third photoacoustic signal, and
applying at least the amplitude of the first photoacoustic signal and the amplitude of the third photoacoustic signal to the linear spectral unmixing model;
wherein the linear spectral unmixing model is represented by:

$$sO_2 = \frac{\varepsilon_{\lambda_3}^{de} - r\varepsilon_{\lambda_1}^{de}}{\left(\varepsilon_{\lambda_3}^{de} - \varepsilon_{\lambda_3}^{oxy}\right) - r\left(\varepsilon_{\lambda_1}^{de} - \varepsilon_{\lambda_1}^{oxy}\right)}$$

where $sO_2$ is the oxygen saturation in the blood, $$r = \frac{\mu_{a3}}{\mu_{a1}} = \frac{P_3 F_1}{P_1 F_3},$$

$P_1$ and $P_3$ are the amplitude of the first photoacoustic signal and the amplitude of the third photoacoustic signal respectively, $F_1$ and $F_3$ are optical fluences associated with the first and third laser pulses, $\varepsilon_{\lambda_{1,3}}^{de}$ and $\varepsilon_{\lambda_{1,3}}^{oxy}$ are molar extinction coefficients of oxyhemoglobin and deoxyhemoglobin at the first and third wavelengths.

36. The method of claim 35,
wherein the first, second, and third laser pulses are transmitted to the human or animal sequentially, a time difference between transmission of the first and second laser pulses is in the order of micro-seconds or nano-seconds, and a time difference between transmission of the second and third laser pulses is in the order of micro-seconds or nano-seconds; and
wherein the first, second, and third laser pulses are provided by an optical processing unit operably connected with a single pulsed laser source.

37. A method for determining oxygen saturation in blood of human or animal in vivo based on photoacoustic imaging or sensing, comprising:
receiving a first photoacoustic signal, a second photoacoustic signal, and a third photoacoustic signal from a human or animal in response to transmission of a first laser pulse, a second laser pulse, and a third laser pulse to the human or animal, the first laser pulse has a first wavelength, the second laser pulse has a second wavelength different from the first wavelength, the third laser pulse has a third wavelength different from the first wavelength and the second wavelength; and
processing the first photoacoustic signal, the second photoacoustic signal, and the third photoacoustic signal based on a linear spectral unmixing model to determine oxygen saturation in the blood of the human or animal;
wherein the processing includes:
determining at least a first amplitude of the first photoacoustic signal and a third amplitude of the third photoacoustic signal, and
applying at least the first and third amplitudes to the linear spectral unmixing model;
wherein the linear spectral unmixing model is represented by:

$$sO_2 = \frac{\varepsilon_{\lambda_3}^{de} - r'\varepsilon_{\lambda_1}^{de}}{\left(\varepsilon_{\lambda_3}^{de} - \varepsilon_{\lambda_3}^{oxy}\right) - r'\left(\varepsilon_{\lambda_1}^{de} - \varepsilon_{\lambda_1}^{oxy}\right)}$$

where $sO_2$ is the oxygen saturation in the blood, $$r' = \frac{P_3 F_1}{P_1 F_3} \cdot \frac{1}{1 + AP_1 e^{-(\tau_\alpha + bv)2\delta t} + AP_1 \frac{F_2 \mu_{a2}}{F_1 \mu_{a1}} e^{-(\tau_\alpha + bv)\delta t}},$$

$P_1$, $P_2$ and $P_3$ are the first, second, and third amplitudes, $F_1$, $F_2$, and $F_3$ are optical fluences associated with the first, second, and third laser pulses, $\delta t$ is a time delay between the first and second laser pulses, as well as a time delay between the second and third laser pulses, A, $\tau_\alpha$, and b are coefficients independent of flow of the blood, $\mu_{a1}$ and $\mu_{a2}$ are optical absorption coefficients associated with the first and second laser pulses, $\varepsilon_{\lambda_{1,3}}^{de}$ and $\varepsilon_{\lambda_{1,3}}^{oxy}$ are molar extinction coefficients of oxyhemoglobin and deoxyhemoglobin at the first and third wavelengths.

38. The method of claim 37,
wherein the first, second, and third laser pulses are transmitted to the human or animal sequentially, a time difference between transmission of the first and second laser pulses is in the order of micro-seconds or nano-seconds, and a time difference between transmission of the second and third laser pulses is in the order of micro-seconds or nano-seconds; and
wherein the first, second, and third laser pulses are provided by an optical processing unit operably connected with a single pulsed laser source.

39. A system for determining oxygen saturation in blood of human or animal based on photoacoustic imaging or sensing, comprising:
one or more processors arranged to:
receive a first photoacoustic signal, a second photoacoustic signal, and a third photoacoustic signal from a human or animal in response to transmission of a first laser pulse, a second laser pulse, and a third laser pulse to the human or animal, the first laser pulse has a first wavelength, the second laser pulse has a second wavelength different from the first wavelength, the third laser pulse has a third wavelength different from the first wavelength and the second wavelength; and
process at least one of the first photoacoustic signal and the second photoacoustic signal, and the third photoacoustic signal, based on a linear spectral unmixing model to determine oxygen saturation in the blood of the human or animal;
wherein the one or more processors are arranged to perform the processing by, at least:
determining at least an amplitude of the first photoacoustic signal and an amplitude of the third photoacoustic signal, and
applying at least the amplitude of the first photoacoustic signal and the amplitude of the third photoacoustic signal to the linear spectral unmixing model;
wherein the linear spectral unmixing model is represented by:

$$sO_2 = \frac{\varepsilon_{\lambda_3}^{de} - r\varepsilon_{\lambda_1}^{de}}{\left(\varepsilon_{\lambda_3}^{de} - \varepsilon_{\lambda_3}^{oxy}\right) - r\left(\varepsilon_{\lambda_1}^{de} - \varepsilon_{\lambda_1}^{oxy}\right)}$$

where $sO_2$ is the oxygen saturation in the blood, $$r = \frac{\mu_{a3}}{\mu_{a1}} = \frac{P_3 F_1}{P_1 F_3},$$

$P_1$ and $P_3$ are the amplitude of the first photoacoustic signal and the amplitude of the third photoacoustic signal respectively, $F_1$ and $F_3$ are optical fluences associated with the first and third laser pulses, $\varepsilon_{\lambda_{1,3}}^{de}$ and $\varepsilon_{\lambda_{1,3}}^{oxy}$ are molar extinction coefficients of oxyhemoglobin and deoxyhemoglobin at the first and third wavelengths.

40. The system of claim 39, further comprising a photoacoustic imaging or sensing apparatus having a probe arranged to transmit the first, second, and third laser pulses to the human or animal sequentially,
wherein a time difference between transmission of the first and second laser pulses is in the order of micro-seconds or nano-seconds, and a time difference between transmission of the second and third laser pulses is in the order of micro-seconds or nano-seconds.

41. The system of claim 40, wherein the photoacoustic imaging or sensing apparatus further comprises:
a pulsed laser source;
an optical processing unit operably connected with the pulsed laser source, the optical processing unit being arranged to process pulsed laser received from the pulsed laser source to provide laser pulses of different wavelengths; and
at least part of the one or more processors;
wherein the probe is operably connected with the optical processing unit for transmitting the laser pulses to the human or animal.

42. The system of claim 41,
wherein the pulsed laser source is arranged to provide laser pulses of the first wavelength;
wherein the laser pulses of different wavelengths are temporally separated laser pulses; and
wherein the optical processing unit includes:
a first optical processing sub-unit arranged in a first optical path, arranged to provide a pulse laser of the first wavelength;
a second optical processing sub-unit arranged in a second optical path arranged to provide a pulse laser of the second wavelength different from the first wavelength; and
a third optical processing sub-unit arranged in a third optical path arranged to provide a pulse laser of the third wavelength different from the first and second wavelengths.

43. A system for determining oxygen saturation in blood of human or animal based on photoacoustic imaging or sensing, comprising:
one or more processors arranged to:
receive a first photoacoustic signal, a second photoacoustic signal, and a third photoacoustic signal from a human or animal in response to transmission of a first laser pulse, a second laser pulse, and a third laser pulse to the human or animal, the first laser pulse has a first wavelength, the second laser pulse has a second wavelength different from the first wavelength, the third laser pulse has a third wavelength different from the first wavelength and the second wavelength; and
process the first photoacoustic signal, the second photoacoustic signal, and the third photoacoustic signal based on a linear spectral unmixing model to determine oxygen saturation in the blood of the human or animal;
wherein the one or more processors are arranged to perform the processing by, at least:
determining at least a first amplitude of the first photoacoustic signal and a third amplitude of the third photoacoustic signal, and
applying at least the first and third amplitudes to the linear spectral unmixing model;
wherein the linear spectral unmixing model is represented by:

$$sO_2 = \frac{\varepsilon_{\lambda_3}^{de} - r' \varepsilon_{\lambda_1}^{de}}{\left(\varepsilon_{\lambda_3}^{de} - \varepsilon_{\lambda_3}^{oxy}\right) - r'\left(\varepsilon_{\lambda_1}^{de} - \varepsilon_{\lambda_1}^{oxy}\right)}$$

where $sO_2$ is the oxygen saturation in the blood, $$r' = \frac{P_3 F_1}{P_1 F_3} \cdot \frac{1}{1 + AP_1 e^{-(\tau_a + bv)2\delta t} + AP_1 \frac{F_2 \mu_{a2}}{F_1 \mu_{a1}} e^{-(\tau_a + bv)\delta t}},$$

$P_1$, $P_2$ and $P_3$ are the first, second, and third amplitudes, $F_1$, $F_2$, and $F_3$ are optical fluences associated with the first, second, and third laser pulses, $\delta t$ is a time delay between the first and second laser pulses, as well as a time delay between the second and third laser pulses, A, $\Sigma_\alpha$, and b are coefficients independent of flow of the blood, $\mu_{a1}$ and $\mu_{a2}$ are optical absorption coefficients associated with the first and second laser pulses, $\varepsilon_{\lambda_{1,3}}^{de}$ and $\varepsilon_{\lambda_{1,3}}^{oxy}$ are molar extinction coefficients of oxyhemoglobin and deoxyhemoglobin at the first and third wavelengths.

44. The system of claim 43, further comprising a photoacoustic imaging or sensing apparatus having a probe arranged to transmit the first, second, and third laser pulses to the human or animal sequentially,
wherein a time difference between transmission of the first and second laser pulses is in the order of micro-seconds or nano-seconds, and a time difference between transmission of the second and third laser pulses is in the order of micro-seconds or nano-seconds.

45. The system of claim 44, wherein the photoacoustic imaging or sensing apparatus further comprises:
a pulsed laser source;
an optical processing unit operably connected with the pulsed laser source, the optical processing unit being arranged to process pulsed laser received from the pulsed laser source to provide laser pulses of different wavelengths; and
at least part of the one or more processors;
wherein the probe is operably connected with the optical processing unit for transmitting the laser pulses to the human or animal.

46. The system of claim 45,
wherein the pulsed laser source is arranged to provide laser pulses of the first wavelength;
wherein the laser pulses of different wavelengths are temporally separated laser pulses; and
wherein the optical processing unit includes:
a first optical processing sub-unit arranged in a first optical path, arranged to provide a pulse laser of the first wavelength;
a second optical processing sub-unit arranged in a second optical path arranged to provide a pulse laser of the second wavelength different from the first wavelength; and
a third optical processing sub-unit arranged in a third optical path arranged to provide a pulse laser of the third wavelength different from the first and second wavelengths.

* * * * *